US009862935B2

(12) United States Patent
Shin et al.

(10) Patent No.: US 9,862,935 B2
(45) Date of Patent: Jan. 9, 2018

(54) BACTERIOPHAGE AND ANTIBACTERIAL COMPOSITION COMPRISING THE SAME

(71) Applicant: CJ CHEILJEDANG CORPORATION, Seoul (KR)

(72) Inventors: Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 217 days.

(21) Appl. No.: 14/770,420

(22) PCT Filed: Feb. 24, 2014

(86) PCT No.: PCT/KR2014/001476

§ 371 (c)(1),
(2) Date: Aug. 25, 2015

(87) PCT Pub. No.: WO2014/133289

PCT Pub. Date: Sep. 4, 2014

(65) Prior Publication Data

US 2016/0083696 A1 Mar. 24, 2016

(30) Foreign Application Priority Data

Feb. 27, 2013 (KR) ........................ 10-2013-0021498

(51) Int. Cl.

| | |
|---|---|
| ***A01N 63/00*** | (2006.01) |
| ***A61K 35/76*** | (2015.01) |
| ***C12N 7/00*** | (2006.01) |
| ***A23K 20/195*** | (2016.01) |

(52) U.S. Cl.

CPC ............... *C12N 7/00* (2013.01); *A01N 63/00* (2013.01); *A23K 20/195* (2016.05); *A61K 35/76* (2013.01); *C12N 2795/10221* (2013.01); *C12N 2795/10231* (2013.01); *C12N 2795/10233* (2013.01)

(58) Field of Classification Search

None

See application file for complete search history.

(56) References Cited

U.S. PATENT DOCUMENTS

| | | | |
|---|---|---|---|
| 6,485,902 | B2 | 11/2002 | Waddell et al. |
| 8,021,657 | B2 | 9/2011 | Bruessow et al. |
| 2002/0090356 | A1 | 7/2002 | Waddell et al. |

FOREIGN PATENT DOCUMENTS

| | | | |
|---|---|---|---|
| KR | 10-2009-0021475 | A | 3/2009 |
| KR | 10-0910961 | B1 | 8/2009 |
| KR | 10-2011-0041670 | A | 4/2011 |

OTHER PUBLICATIONS

International Search Report dated Apr. 28, 2014 of PCT/KR2014/001476 which is the parent application—5 pages.

Cha et al., "Effect of Bacteriophage in Enterotoxigenic *Escherichia coli* (ETEC) Infected Pigs", J. Vet. Met. Sci., 2012, vol. 74, No. 8, pp. 1037-1039.

Jamalludeen et al., "Evaluation of bacteriophages for prevention and treatment of diarrhea due to experimental enterotoxigenic *Escherichia coli* O149 infection of pigs", Veterinary Microbiology, 2009, vol. 136, pp. 135-141.

Begum et al., "Isolation of a bacteriophage specific for CS7-expressing strains of enterotoxigenic *Escherichia coli*", Journal of Medical Microbiology, 2010, vol. 59, pp. 266-272.

Jamalludeen et al., "Isolation and characterization of nine bacteriophages that lyse O149 enterotoxigenic *Escherichia coli*", Veterinary Microbiology, 2007, vol. 124, pp. 47-57.

English Abstract of Cislo M, et al., "Archivum Immunologiae et Therapiae Experimentalis", Ther. Exp. 2:175-183, 1987.

Sung Hoon Kim et al., "Bacteriophage, New Alternative Antibiotics", BioWave; Biological Research Information Center, BRIC, 2005, vol. 7, No. 15—10 pages.

Mason, "Transgenic plants as vaccine production systems", Trends in Biotech, 1995, vol. 13, pp. 388-392.

Eu Chul Hong, "The Additive Effect of Egg Yolk Antibody in Early Weaned Pigs", Master's Thesis, Dankook University, 2001 in 66 pages.

Chinese Office Action dated Jun. 29, 2017 of corresponding Chinese Patent Application No. 20148001093T5—9 pages.

Dai, "Identification of *Escherichia coli* K88 phage, preliminary identification of classification and determination of biological characteristics", China Master's Thesis Full-text Database Agricultural Science and Technology, Dec. 15, 2009, pp. 8-10, and its English abstract downloaded from http://cdmd.cnki.com.cn/Article/CDMD-11117-2009192845.htm—7 pages.

*Primary Examiner* — Karen Cochrane Carlson
*Assistant Examiner* — Jennifer M. H. Tichy
(74) *Attorney, Agent, or Firm* — Knobbe Martens Olson & Bear LLP

(57) ABSTRACT

Provided is a novel bacteriophage ΦCJ20 (KCCM11362P). In addition, the present invention relates to an antibacterial composition including the bacteriophage ΦCJ20 (KCCM11362P) as an active ingredient. Further, the present invention is a method of preventing and/or treating infectious diseases by enterotoxigenic *Escherichia coli* in animals except for humans using the bacteriophage ΦCJ20 (KCCM11362P) or the antibacterial composition containing the bacteriophage ΦCJ20 (KCCM11362P) as an active ingredient.

10 Claims, 3 Drawing Sheets

SEQUENCE LISTING

<160> NUMBER OF SEQ ID NOS: 3

<210> SEQ ID NO 1
<211> LENGTH: 35693
<212> TYPE: DNA
<213> ORGANISM: Artificial Sequence
<220> FEATURE:
<223> OTHER INFORMATION: a novel Enterotoxigenic Escherichia coli specific bacteriophage KCCM11362P

<400> SEQUENCE: 1

```
gtgaccgtca tgacggaatt tatgtctata aagggaccaa gaaaattggt ctcatgactg     60

acttgcggaa aaaactcgcc tccaataaaa agttgaaggc gaaacaaaaa gaatatcgcg    120

ataaaaaatc agaagagcgg aaagaagcac tgcatgaatc tgttcctgaa atggttgact    180

tcttaaagaa ccatttggtt aaatatgatg cagaagtgtt catcaatcag acccaaccta    240

atgtgcatat caatggatgt gtttgttatg ttgtggttga acccctgaca cttcaacacc    300

gcctgggaat taaacaccca gtgttaaccc aggatgatat ggcggatgaa gttggtaatc    360

agttccgcat ttcagcatct gacagtacaa atcacatcct cctgaatggt ttatcccagg    420

atgatattgt tgaggtaatc atcaagttat gcaaataagt aatctcactg cagggcttat    480

gctcgccctg atagtaactg ctggtagtgg tttctatcta aaagcaaaag tggataatct    540

caagacagcg gtggcggaag tcaccaaagt cgcagaagat aatgcgaaaa atctgcaatc    600

agtaaaagac caggttaatc aaattaatct ccttgaccaa cagcgccagg aatatgttga    660

actcctgcag aaggaaaatg ataaacttcg cgcagatgca aaacgtgcta aggttgtggc    720

tgcgaagcct aaattagttg aaaaacagat taatcagtca tttgataagt tcgcccagga    780

cttccaggag ctcaccaaat gatgaaatct atcatggcag tatgtttggc tattggactc    840

gtttcatgcg cccagaagcc cgttgtggag cccacaatcc aagttcatcc taattggcct    900

gttgcattgg ctgattacaa acagcaatgg gaagttaagg taattgatgg tcaagtctgg    960

gttggtatgc cttttgaagc atcgcaagaa ttcaggattt ggatgaatga tgtaaaaagg   1020

tatgtacatg accaaaaagg tatgttatgt tattatcgtt ctgaactaaa agaggaacgt   1080

tgcaaatgat tgagtcttgt atcgatgggt cggatgtcat tctatttggc tttacatgct   1140

tttgttttgg aatcgtgctt agcatgtgta taaatggtat ttttggaaag tagtttacaa   1200

actcttggga gcagagtata atgctcctac ggattataaa atttgaggaa atgactatga   1260

cattacgtga taacagtttt gtggctaagc ctgaatacat ttcaggtgtt aaatcccctg   1320

cattacaaaa gctcttaaaa ttagggtcct gtgcaagtac accaattgaa aagaaggcaa   1380

cttttgattt tgcttgggct atggtggacg gtattgatgt agtaagacag gtaacttttt   1440

atgctccggg cgctattaag ccttcgcaaa ttattaatct ggatggaagt aattatatta   1500

ctattcagca ttggtatcgt atgatgcgac ctgtttggga atacccggaa tttattgaag   1560

aatacaatga aaaagaacgt attcgtgagc tagtaaaaag ttttgaatac gcggctaaac   1620

gccatggtca aatgcaatct gccgctgcac ttggtgatgt ttctgaaagt gcagcttatg   1680

aaactggtaa aatccttaaa acctgtcgcg aagaacttta taaggagctt ggcgtatgaa   1740

agagttatta gagaattaca tcaagtgttc agacaattat attgattcat gtcgcggcgc   1800

tgtatatttg gatttggacc gcggaatggt attgaatgat gaagaccctg caaaagcctt   1860

agatgatgca ggcaaagctc tacgtaaagc ggcaaaagct caaggcgtgg atatgggtga   1920

gctaaagaat catttaatta tgttcatctc tgcaaatact cgccgcaagt caagcaataa   1980
```

```
ggcagtagct gaattaaatg aagggcgtgt tgaattgcgt attcagcttc ttaaaactct   2040
gttaggaatt aaatgatgaa gagaattatt ctgactgttg gttgtcctgg ttccggcaag   2100
agtacctgga cgcgtgaatt catcgctaag aaccctgggt tctttaatat caaccgagat   2160
gattatcgtc aatccattat gggtcatgaa gcccgtgatg aatacaaata ctccaagaag   2220
aaagaaggca tcgttacctg tatgcagttt gatgcagcga agggtatttt gtatggcggt   2280
gattctgtta agggtgtaat tatttcagac accaacttga atcctgaacg ccgtttgatg   2340
tgggaaacct ttgctaaaga atacggctgg aaagttgaat ataaagtatt tgatgttcct   2400
tggactgaac tggttaaacg caacaatcgc cgtggtccaa aagcggtacc aattgatgtt   2460
ctgcgttcca tgtatggtca tatgcgtaca ttccttggtc ttcctgttta taaaggaact   2520
cctggtcaac caaaagccat tatctttgac ctggacggaa cattggcttt gcatgtggct   2580
cgtgggccat ttgagcttgc aaaactgtct actgatgcac caaacgaaat ggttgttcag   2640
tacctgaaaa tgcttcatca cgcagggtat agtattatca cagtatccgg gcgcgaatct   2700
ggtaccgaag aaaatccaac ggaatattat gaagccacca aagcctggat ggataagtat   2760
gaaattcctt gggaaactca tatccagcgc gagcaaggtg acgaccgtaa agatgatatt   2820
gtgaaggaag aaatcttctg gaacaaaatt gcaccacatt atgatgtgaa attagcagtt   2880
gacgaccgca gtcaagtcgt tgagatgtgg cgtcatattg gtgttgaatg ctggcaagta   2940
gctcacggtg acttttaatg aataatatcg aaaagatttt tcgtacaatc gaagaaattg   3000
aaaaacgtaa atgctttttc ttcggagtat ggcctttaac tgatggacgt attggcctgg   3060
atgttatgga ctataaagat gaagacaagg tcgatggtgg tatttttaaa tccgctccag   3120
aactcttagc cttcttggaa gaacattatg tataacaaac accatgaagt tgaagaagaa   3180
gcttataaag agcttcagaa actggtaggg cagaatatgt ctcctgctct tatcaacaac   3240
ctggctgcac tgcgcaatga tatcaacgaa cgatacaagg gcgaatatta tgttgaattc   3300
gttccgctga ctgaagtcat tgaccgattt atcgttaatg tcaaggtgca taccgtccat   3360
taacgcttta aaaattttat gttataatgg ggtctaggtc ctttggatac cccaataact   3420
aagcgagaaa agaaatgttt cctacatatt ctgaaattgt taaagtagtt tttagtcaga   3480
ttgtatctga ttatctatac gaaagcgtcg acgtgtcgac tgaactaaag gtgcatggtc   3540
gtttgtctgc tattctggaa atcatgttcc cggatgcagt tgatgcaatc actgttcaac   3600
tcacgcctgg cgcagcattt gcaattgttc catttaaaat tgataaccac attttggcta   3660
tttcatgcaa aatggacttc cagaaacaaa cggtagttgt cgaagcaatt taagtgttta   3720
ctttcaccac ggatggtgta taatgaattt catcaacaca tgaggaaaac aaaatgagta   3780
atttctttga agaaggaaag ttttacaagt tcgcatctga aaattgccaa aaaacagttt   3840
attgccggag gctgggcagc taattaccaa attgccaaat acatcggtat gactccgttt   3900
gaagtgaaaa ttgtacctga taccgcgaag cggtggaaga aaagtttgtg agattcgttt   3960
gattgatgaa aagaattttg tggatttggc aaaaaatatct ggtgcacaga acaggcatca   4020
tggagcaatg tttgtttctg ctggtccatt gtctgatgaa tttgattatt tcatccaagc   4080
ggaagttggt gttaagccag aagttgaacc tgtgccagtg aaacttgcat cagtttggaa   4140
attgcttgtg gttaaaaatg gcaagattga gattaactct cgtcatgtgt caaaagaata   4200
tgcggaaggc gaagcagagc gtctgttaaa ccgtggtact gttgaagatt gctatattat   4260
caaaggcgat atcacaaaag cttctatcat taaacaagta aaacaggaga caatctgatg   4320
cttagcgaaa ccccaattac tgttgaagag ttccacgaaa aagtgaaggc atttgctcaa   4380
```

```
gcgatgatta atcgcgtatc agagcgattc cctgctgcga ctttgcaagt tattcaggaa   4440
tctgcacgca gttttatgat tgtcattaat ccgaaaatta ctctaaaagg tggtgaccaa   4500
ttgacccaac tgaaattggg ttctgacggt ctggttgaag cgcagcgagt gtatattcaa   4560
tgatgaattt aatggatatt ttcaaagaag cacttaaaaa tgatttaggt gaccatcgta   4620
agttggaccc agaaacaact gcatttatca aagtaacgct tgcaaatgat gctctgttta   4680
aaagtattca cccaagtaat tatgatgcgg ttgttattac agaagctcct gtagaaattg   4740
gtgagcgaat gtttggggtg atttttggcg ataagaaaaa acgcttcagc gacggtgata   4800
gtataattac aacacatgtt aagagcatta ctaaattgcg acatgaatta tatcgtgttg   4860
aaactattaa aaccaattat ctcgtggtga tgtaaatgaa accaactact gttctgcaaa   4920
tcgcatacct tgtatctcaa gaatcaaaat gttgctcctg gaaagtggga gctgttattg   4980
aaaagaatgg ccgcattatt tctacagggt ataatggttc ccctgcaggt ggggttaact   5040
gttgcgagca tgcggaagag caaggttggt tactgaataa acctaaacct gttctcgtcc   5100
ctggacataa gccagaatgc gtgagattcg gtcaggttga ccgttttgta ttggcgaaag   5160
ctcatcgcga agaacattct gcatggtcaa agaacaacga aattcatgcc gagcttaatg   5220
cgattctgtt tgcagccaga atgggttcat caattgaagg cgctactatg tatgtgacgc   5280
tttctccttg ccctgattgt gcaaaggcaa tttctcaatc aggaatcaag aaattggttt   5340
actgtgaaac gtatgataag aatattcctg gttgggatga tatcctgaag aatgcaggaa   5400
ttgaagtgtt caatgtgcct aagcgtagtc tagacaaatt gaactgggaa aacattaacg   5460
aattttgtgg tgaataatga aatttcgtct agttaaattt tcagggctaa actcaaaagg   5520
cgaaagctta gtagcctatt cagtagaata caaaaagtac tttttctctc gctggaaatc   5580
gtactataaa tccgagtggg ttcgcgccga aacgaactat aaaacggtgc ctattcttga   5640
aaattgtcac catctattgc gtgctctaaa agagcgtaat gcaaccacta ttaaaactgt   5700
tttggaataa ttatgatttt aactgaacaa gaaacaattc gtcttcgtga aaaagtcaag   5760
actatcttgt ctgttggctt tcatgaagtt ctgtttgaaa aagcagatgg cagcgttcgt   5820
cgtatgactt gtactcgcga cctggacctg cttccatata aagaaatcca gacccctgga   5880
ccagaagctc ataaagaacc agttagctat atccgggtat ttgataccaa gcttaatgaa   5940
tggcgttcat tctgtttcaa taaattgatt tccgtgaatg ggctacagac cgagactctg   6000
cttgtccttt aatgcttcaa acggtgcgtg ttattattaa tacatgacca aacaacatgg   6060
attaaatatg gaattaccaa ttaaagcagt aggtgaatat attattttgg tttctgagcc   6120
aaagcaagct ggtgatgaag aaactacggc atcaggtatc gttatcggaa aactccatca   6180
gggtgaaatc ccagagatgt gtgaagtatt ttcggttggt ccagatgttc ctgaaggttt   6240
ctgtgaagta ggtgatttga ctcctcttcc ggttggcaag attgcaaacg ttccacatcc   6300
tctggttgct ctgggactta agcaggctaa agaagttaag cagaaatttg tgacctgcca   6360
ttataaagct gttccttgtc tttataagta aaattagcgt tataaataat aatatggatt   6420
ggttgatgtc atacagagct ttgctggtgt atggggttag ctaatcctaa acggtggact   6480
acaactgaga gacttgccgc aaggaagtga aattcagaag aacgtgtcca ccaaatattc   6540
acctcatatt gaggcttcta aaatgtcttt aaacaaacaa ttacaacacg ctctcgaact   6600
gcaacgcact gcatggaata acggtcacga aaactacggc gcatctattg atgttgaagc   6660
cgaagcactg gaaattctgc agtatttcaa acatcttaac ccggttcaaa ccgaccttcg   6720
```

-continued

```
cgcagtgctc gaagcaaaag atgaactgaa atttgctaag ccgctggcat ctgctgcccg   6780

taaagctgtt cgccattttg tcgtaaccct gaagtaagct gtaggtgatt cgctacctta   6840

gtgcggctag aaaatcgagg agccgtcgaa ctgcctgatt aatgattcgc gaatcattat   6900

agttttaaga ccccagcagt tttacggtgt acctcttgaa tgtattttgt actatcacgc   6960

gtcagaaaaa ggttatctgt ctaagccgtg gttggtatga tgacgaggtt tatggttatc   7020

ctgtcgttaa atatccgaaa cctaatgttc ccttcgaggg cttgcgcagg caacgtcaat   7080

aagtcctgca ttctatttta aagagaattt aatatggcta agaaagaagt taaagttgtt   7140

gatggctcct ccaaacgcgc tggttacaag cgtgcgtcca acaagcgaat caatcaggta   7200

actgataaac ttcaggctcg tgctcgtgcg gtattgcgtg ccgatgcagc ttgctttggt   7260

aagccgaaag cataagttca gggactcttc ggagtccctt ttttattttc cataaagggg   7320

tttacaacag ggtttgacca gtgcataatg attccatact gagttacaca ataaaacact   7380

ggagaataaa atgaaaatca atcttaactc atacatcaaa ggtaaagacc acgacggtta   7440

caaagccatt gaaactaaag aaatgcaatg gcacttgtat aaagaacagt ttgaattcgt   7500

ttcttgtatg actccagaag gtccttctga tgacttctcc tggaaaatta tggtaacaaa   7560

ctttttact ggtgatacct acgaactgaa aactttgatt cttggcaaga ttcgttgtaa   7620

gacctatgaa gatgaagaaa ctggttattc tgaagatgtt acatggtatc aaaatggtcg   7680

caccactgct gatgatttga ttgaaaaaat gaaagctaag ggtgaattaa atttagataa   7740

ttggattaaa gtcgcataaa acagtttact ttggtacagg ttatgatatt atagacctgt   7800

accaacaaat gaaaacaact ggagaataaa atgaactaca tcaactttga acgcaaatat   7860

gtttctaact gcatcccagg ttcttctgaa gttatttgcc tgtggaaaca taaaaatggt   7920

tcagtgtgcg aaattgaaca gtatatgact cctaactacg tttatatgcg atttgaaaat   7980

ggtatcactc tttcaatcac tatgaccggt tcaaccttta aaattgcttt agatgatgat   8040

ttccgtgaac gtgatttagg gactcatcct tgctggaatg gtgttaatcg caagccgttg   8100

gttaaaactt ggattcgtca tatcctgggt aacaaagcaa aacctgaaca cctggaagca   8160

atctttgatg tagttcttaa tgaatttgat atctaatctt aaacggggcg aaagcccctt   8220

gaggaaaata ctatgtttat gactacttac tttgatacac gtaaaaattt ctgtgaagtt   8280

gtcttttcta aagcaagccc aggcgtacct gctgataagc aaccaactaa agaatccatt   8340

aaaaactatg cggatatagt ttgcccagtt gaattcagga ctgttaatgg acgtgatact   8400

ctggcaatca ccaagcttag ccgcgacatt gatattgacc caattgcagc acgtgaagtc   8460

aattcgtctg atattaatgg cggtaatgtt aaatcacacg gtttccagat gaggttctaa   8520

tgaaactatt tctatcgcaa accgtccagt taaaaggcgt aggtattcct ggaatgattt   8580

ctaaggtctt gcctgctttt caattaggca atatttccat taaagaagca tatgcagtcc   8640

tgtgggttga cggaacagaa gacgttcgca tgggtggtga gttgtctgta atcaaatgtt   8700

taaagcgagg ataatatgtt taagaaactg attcagaaaa ttttgggaac agaaatggtt   8760

gaagttactt atcgcgtaac tgacgtgagt ccatgggccc gaaatattga accatatact   8820

aaaacaatta aaatgctgaa atctgacggt ggattatcta ttaaagaccg tctacctggt   8880

tatggtcatt gggctgatgt agatattatc agcgtcaaag atatttaagg aaccttcatg   8940

attaagaaat tatttaaaaa gctgtttggc ttggaaatgg ttgaagttac ttatcgtgtt   9000

attgatttat cacctccata tgcttgtgat gaagatgcta ttaagactgt tgtaatgcga   9060

aaaacatatc gcgggcggtc aattaaatcc agattaccgg accacggtat gtggtatgca   9120
```

```
accaagatta tcagtgtcaa agatgtctga gttagaaatc agaagcaatt tcccatggcc   9180
gtcatgtgca ttaagtaact ttgctaaacg gccttttgtt atggagggca tccagtttgg   9240
gggtcttgaa ggcttccttc aagggtgtaa ggtgaaaaat catgaacaac aaaaacgtat   9300
atttgggatg tccggcttgg ccgcccagca aagtggaaga gcttatgcaa gagctgcgga   9360
ccgtgggacg cttttctggc ttggaattcc cttttcaaga tactctgcag catggaaaga   9420
gttgtataca aatgcatatt ttgaagcagc gctccaaaac agagggtttc gcgatgcgtt   9480
acaatccaca aaaggcaaag ttttaaagca ttcgatggcg agccacctta ctgttcatga   9540
tacaatattg actgaacaag aatttattga catacttaac caattgagag atgcattatg   9600
aaacccgtta ttttaacaga tattgatggc gtatgtttgt catggcagtc aggcttgcct   9660
tatttcgccc aaaaatacaa tttacccctg gaacatatcc ttaagatgat tcaggatgaa   9720
aaatttgtga cccctggtaa actgttcaat tgtgatgaag agttgggagc acagttgatt   9780
gagaaatata actgttcaga ttttattcgc tatttgtctc cttacgcaga tgcgttaagg   9840
gttattaata acctcaaaga gcaatatgat tttgtggctg ttactgccct aggtgattcc   9900
attgacgccc gtctgaatcg tcaattcaac ctgaatgctt tgttccctgg tgcatttaaa   9960
gaagtgatga tgtgtggcca tacagcctct aaagaagagt tattccagaa agcgaagacc  10020
aaatataatg tcgtttgtta tattgatgac cttgcacacc attgcgacca tgcgagtgaa  10080
atccttgaag tcccggttta ttggatggcc cgtggcgaac gtgatgctat tcctaaaaca  10140
gcttccaaag tttttaattg ggacgatatt gctggacagc ttaaactgaa acacaaagat  10200
gaaccagtca aaccagaatt cacccctgat gaactccgta aactggaaga gttgtttcgt  10260
gaaactcgcc gtcttcaaca acaaatgcaa caaggctggc agccaggtca accatggacc  10320
cctggatata atccagcata tccatatcaa tatggcccac gcgtaggtac tggcattgaa  10380
tattggtaca atcaaccgac tggtggccaa gggggtaatt gatgtttgtc gttcatacta  10440
tttctgatta cggtcctact actaccatgg attatggcca tgttaatcag tttattcgtc  10500
atgtgaatca tgattactcg tttgatatta acccagccaa agaccatccg gtttggcgtg  10560
aatgtgttga gcaagggttt atctatgttc actttatgtc taagtttaaa ccagatgggc  10620
gaatgagatt tgtgttcact tatcacaaac gcctggattt gcttttggaa gatgtggcat  10680
ataatagagc caacgactaa gaggtgatta tgattttaga tattttaaat gaaattgctg  10740
caaccgattc cactaaagag aaacaagcta tcctggaatc atattctgac aatgaaaccc  10800
ttaaacgcgt gtatcgtttg acatattcca aaggcatcca gttctatatt aagaaatggc  10860
caaaacctgg gacaacgact caaagctttg gtatgctgaa tatcgatgat atgcttgact  10920
ttatcgaatt cacattagcc tctcgtaaat taacaggtaa tgctgcaatc gaggaattat  10980
ctggctatat tgctgatggt aaaaaggctg atgttgaagt cctgcggcgt gttatgatgc  11040
gtgacctgga atgtggggca tccgtatcaa ttgcaaataa ggtttggaaa ggtttaattc  11100
ctgaacaacc gcagatgctc gcttcttcct atgatgaagc cggtattgcc aagaacatta  11160
agttcccggc ctttgcgcaa ttgaaagccg acggcgctcg gtgttttgca gaagttcgtg  11220
gcgatgagtt ggatgatgtt cgattgttat cccgagctgg caacgaatac ctcaagcttg  11280
accttcttaa aaaggaattg attgaagcta cccgtgaagc gcgtgagaga catcctgagg  11340
gcgttttgat tgacggtgag ttagtatatc atgaacagaa aatagctccc cagaatgacg  11400
gtttgggctt cctttttgac gattcagatg agattgcccc tgcacaagaa actgcggaat  11460
```

```
caagaacctt ttcaaatggt ctggcaaaca aatcattgaa aggaactatt tcggcagcag  11520
aagcttcttg catgaaattc caggtttggg attatgttcc gctgattgaa gtctattctg  11580
atgttaagat tctcaatccg ttgaaatacg atgtgcgttt tgctgttctg gaaaaaatga  11640
ttgcagataa cgtggtgctg catggttttg accgcatgat tctgattgaa aaccatgttg  11700
ttaacaatct cgatgaagcg aaggttatct ataagaaata tgtggatgaa ggtcttgaag  11760
gtattatcct taagaacatg gcatcgattt gggaaaacaa gcgctcaaag aacttgtaca  11820
agttcaaaga agtaattgac attgcaatgg aaatcattgg atattacgag cacgataaag  11880
acccggataa gattggcggt gttgtgcttc gttcttcttg tggtaagatt acaaataact  11940
gtggttctgg gtttaaagac acaactcaag ttaaagataa gaaaaccaaa aaatgggtta  12000
ctattccgat tgaggagcgt catgaaatgg accgtgaagc cttgatggtt aaagctcgta  12060
aaggtgaatt ggttggaatg attgctgact gtgaatgtaa tggttggttg acttccgaaa  12120
ctcgtaaaga taatacggtt gcattgttcc tgccgattat caaagggttc cgtttcgata  12180
aagaccatgc agacacattc gaagatgtat ttggcgactg ggcaaagacc gggttaaaat  12240
aacaaagggc ttcggccctt tttagtataa atacatcata ttttataagg aacctattat  12300
gtctgaacaa ttaaatgaac tctttgacaa atatatcgaa gccttcggtt atcctgtcat  12360
taatatgaac ccaaaataca aggtcccaca ggtttggcaa ttcggtgttc ctgggaccaa  12420
ttctcttatg gctcgtttga tgcaattcac gggcaaagaa acagttaaac agtataaacg  12480
cggtgatgca attgccgagg tattcctgct ctccgggact tcacatggcc atgctgttcc  12540
tctgaagggt ggtctaggtg aaaaacctct tgatgcaatt aacctgattt ttgttacagt  12600
gtgggaaagc attaaactgg gcaaacctga tgtagtcttg ttccgtttcc catccaaaaa  12660
gatgaaagga caagaccaag ctgttattcg tattatgaat cgactgattc aaatgaaaac  12720
cagcgggcgt tatcatgttc ttccgaatgc ttctggcctc ggtaaaaaga acgcttatgt  12780
aattatgtac aaaaagggtg ttgacctgct ttcggttgat ggtatgccac cagtccctga  12840
gaaatatcaa aaagttgaaa ctaaagttgg cgatgtattc accaataaag atacaggtgc  12900
tcaagtctcc aaacaagaaa tcgcagccga agttctgatt gacgcagcaa acaaaaagac  12960
cgacgctgct gttgcccaga aaactaaaat cagtcgccga gctattgcac aagcccagta  13020
cgcaccaagt gattccgtgc cagaaggttg ggacgaaatt gatgcagaag ctgctaagtt  13080
tagtcgaccg gctacggcag aacttatcga tgattatgaa gaactggaaa tttttgttcg  13140
accttccgaa acgaatacta tggctcgtat gcgcgcagca gatgaggcta tgcgagcaaa  13200
tggtgtttgg aaagaagaaa ttcgtgttga agactctgac ccaattttta accgtatgca  13260
tcgtgaactt aaacgtgccc ctgttggcag tatgaagcag atgcagattt ttgccgaatc  13320
atgtgccgag attcttaacc ttcgcaaagc tgcatttatc gaaagaaaaa tgaatgatgc  13380
tcctcctaac ctggatgcag ccacttatgc agcctcgctc tgggaaaaag aatacacaag  13440
cgccattcgt gttgcagtta aagactttgc cgaagaagca tcagaaaaca ctcttaattt  13500
cacagcaggg tatactgaca accgtttcca ttatggccag cgagaagcaa ttgcagatta  13560
ttgtggagca aactatgctg atattaataa ttatttgatg ggcaaatatt atgaagaaga  13620
agctgaattc ctaaatctag acagagttgt cgaaacaatt aaggaattgg attcggcctt  13680
tgaaattgga cataagttgc cgcctaatac aactctttgg cgtggtcaat atttaaatgt  13740
tcctacattt gataaaatta agcaatcgaa attattttat ttcaggaact atgtatcaac  13800
gtcgtttaaa ccgattatct ttggtggttg ggtggcgaac gttgctatgg ctgcagttca  13860
```

```
tcaggactat cgtgatggga catctttcca ggctgatgac gaaattgttt taccagatat  13920
gccggatgca cgccgcgacc acgtaatgat gcatgttggt tggaaaattt ctggggcgga  13980
cttaattaac gtaattgttc ctggggaatt gtcaggcaac ccatccgagc aggaagttat  14040
tcttccgcgt ggaactgtag ttaagattac caaaattact gatgcttcgt atcaaggaaa  14100
cgcgaacgtc aaaatgctgg aagctgatat ccagactacg gaccaactgg atgaaaatgc  14160
agttatctat gatggtgatg tgttgatgga aactggtgag cttgtcgttt atcagggcaa  14220
ggaaacagaa gagccagcag aatctgttga ctttgcatcg tttgcatcct ctggggtaac  14280
gaagaaagtc aatcaaggtc ttggtattct tgctagttgt attaatttgg aagctattcc  14340
tcctaaattc ctttcgtagg ggtttacaag cacaaggaag tgcgatacaa tgttcatatc  14400
aattgcacat gaggaaaata aaatgaaatc atcttttcgc tttaatggtc aggaactggt  14460
agttgagaat gttatcccgg cttcagaaga gtttgacagc gcggtgggta atgaactgcg  14520
gcgcgtgttt ggcgaagata agaagtttga ccttcgccct gttgaaaact ttgtaaattc  14580
tgaacaaaca gaaaatattt ttaatggtgt agtaactggg caacttgaat ctgaagcacc  14640
aattgcaatt acagtatttg ttaagaaaga agctgtcatg actgcaacag gtttcatttc  14700
attccgcaaa taaaaaaggg accttcgggt ccctttcttt ttataatata cgttaacttc  14760
tcccagaacc agtaaacgta ttgtatagac ttgttaatcc agattgagca ccagacaagc  14820
gactcaattt ggcaacttct gcgttcaagt tgttatctga actaatacca gatacacctt  14880
taataacctt atcttccaac cattccaatg cagcagctct tcccaccgca ccagttgaca  14940
taacgcgata agcaaaagtt acatcaaatg tagctatctg attatcccct tcatagctca  15000
attcaggcgc tgatacactt acaggaacac aaccggttaa cataacaacc gtatgtggta  15060
acccattacg cgaatgaagg ttaacctgaa tatcagcttc aacgtcttca ggcaaagccc  15120
ttagttgggt aactgggtcc tgtacagagt taacccaatc gttaaatgct ctgaagttcc  15180
ccgcctctga atccattcta aagctcaata ccaacggaga atattctctc cctgttatct  15240
tgatatttgg cgcattatgg ttaaggtcca tttcgtagtt caatgtgtta tccggaagct  15300
taacagagtg aactaataga ccagccgttg gataagccat attaaagaaa tcaagcaggt  15360
aagtaccaac ctcaaattcc cctaataatg attgcacaac acggttactc attgcaccga  15420
taagatattt gcttatccct gatttacgaa taagcttttg tgttccggca gtaacaagag  15480
ttgttatccc ttgagttaag tcaccttgtg ttaatccgaa ccaatctgag ttaacaggaa  15540
ggttgctgaa taatgcgcca ccaaactggt ccagaagatt ctgagattta gaggaaggtg  15600
cggtcgcgaa gaccacacta aaaaggttat tcctttgcaa gtcgatatta atcgcttgtg  15660
tttgaaattc ttgtaaagta aacattagaa accttccgca tataatgagc cacggttaag  15720
cgtaatgatt tcacggaaag tgatttcaag tacaaaagtc gatggcaggt taggagcaat  15780
agccaatcca ccgaaatgac catctgggga tttatcgaat cttatgctct gaatctgaca  15840
cggcccaaat agctccccgc gaccatcata cgagcttgta tcgccaaagt tgcggatata  15900
ccaaatggta gggttagaga ccaccagaac gttcgttagg aagcttgtta tctcttcacc  15960
gagcaacttg ccgtcaaagt tatcgattgc ttccttttttg aaggtggatt tataccatgt  16020
atcgattttt tctttcagct cggaagcaaa cgaactttta ccagtttccc cataggagta  16080
atagttaaaa atctcgtata tcttcactat ctggattaag tcctgggctg aacgtggtgt  16140
catttcccat gtgtaaactt ttgtcctgtt atccgggcca gcgtacatgc ttcttgccgt  16200
```

-continued

```
tgtgtaaatc tgttcaccgt ggtcggccat tacaccgttt gtaactgatt cgagtgcgcc  16260
gaaaactgca gtcgatgcaa tgttactaag aatgccagta gctgagccac cacctttcgt  16320
aataagagac tcaccaacat cgttgaatcg atgcgatacg gattctacat cagacttcga  16380
acgaggcaac aggatatttg caacagcgtt cgaatcaaaa cttttacctg ttgaaccggc  16440
tccggttaat tttgatttag caaaagatgt taaactttta accgggttaa atgaagcacc  16500
gttggaaact ttctttaatg aagtcaattg gcttgacctg tctgagcgta attccggaga  16560
tgttcttgaa ctgaaattgt atgccgtgaa taacagacca tttttataaa ggtcattaac  16620
tcgcatatca tctgaagaat cattaccgga agctcgttct gctggatatt gcgccacaat  16680
agtagcttga gtctgggcag cttttgactg cccagcggag gtcttagaac ctccgttaaa  16740
taaacccgca atatcaatat cgagttcttt tactttcatg ttattcctta gttaattctc  16800
gtggcctgtc tcatgccagg ggcaggggtt gaactttgag gaggcatatt gtattgcgtc  16860
ctggaagtct tctgaatatt attgaccgtg ttaatttgtg cctgagccgg tgcatccttg  16920
tatttatttt ctttggcctt catgccttcg tcaaccttcg cagcttgttg tgcatccgga  16980
gaagtcttaa catccggcgg tttaactttc ggttcgtctt tgaacttctc aagagactta  17040
tcaagttttt ccaacagggc gcgcatattc aggtctttcg gagctccacc ttttgccata  17100
gcagggtcag ctaattgttt ttcaatgtta gctctcattt ccagcgcatt ctttttatcg  17160
gttgcgtctg gcttcattag attgtcggca gtttgggtca aacgaataat atcagcctgt  17220
gctttgtcac gcttcttgaa atagtccaga cgttcttctt ccggaaggtc tctgaagctt  17280
gtgtcaatac cgcctgcgcg aagttggtca gcttgttcct tggtaagatt accatatttt  17340
tcggcttgat taattagttc aggtttatcc ttatacttct tattcatctt ctctgcagct  17400
tccattgctt cagccgaacg tttgtcatga tattttgcta tcttggtttg gtcttcatca  17460
tccagagttg cccctgtatt ttgctgataa gacatcaaag ccgaggcttc cacattatcg  17520
gctaaatcgc ccatcccagg gattttgctt aagatagctg aaatcagttt cgaaatccca  17580
agcataagaa gttgagccat gttcttcgtt aagttgacca tcccacggat aatagcttca  17640
gctaatccca accaattctt ttgactaaac atcgcttcgg cgttcttagc ccaggtcatt  17700
agtccttcga gcaacgggcc ccattctttg aacttattat taaattcaac ccatcctttt  17760
tcgaattgct tcatgaaata ttggaagtaa actcgtatcg catcgatacc gaataccaac  17820
aacaataatc caccaataag cttggctgct tcggctgctg ccgtaattgt atatttgaac  17880
agcatcccgg agattcggtc agctacagaa atcgatgcct taaatccttt ttcggttatc  17940
ttcgaaaggg tatcaagctt atcgccgaga gaccaagtgt tagtctcttt accttctgca  18000
tcattctttg gctgctccgg ttccggtatg aagtctgcct ctggcttttg ttcttcaggc  18060
ggtatgagcg ccggaacgct cgctgtgggc ttattctctt caggctctgg taatgcatcc  18120
tcaacgggtt taaggctttc agaaccagcc acaggagacg tgacgcctat tttaccgctt  18180
atcattgcgc tgagtttgtc gagcttatct gagagaatat ccgtaaggtt tttaatccct  18240
tgttgagtct tctcggtggc ttcggccgtc agttcgaccc cagcactgat atcctggaga  18300
actccattat tggtttggat attctctata atctgattac ccttatcctc aatagcttcc  18360
gatacaagtt cggtcgcagc ctgagtattt gtaagagtcg tattcagatt cgatagttca  18420
tcattctgtt cagcagagag ggcttccgcc ctcctttgtg gtgctaattc ttcgataagc  18480
tttttattcg gtccaccacg tctgaagctc gtttgttcgg agttcttatt catttaggag  18540
ttccattatt ttcagtaacc ccttaacagg accattcggg cccgggattg ctaatgtgct  18600
```

```
tgtgatatcg tctgcccact tagcaacaaa agcaggcata tccagaaagt ctggaacatc  18660
ttccccgaga taaagggtct ccaggagatt gtcaactggt ccgaattctt catacggttt  18720
attggagcgg aatttaaatg tctttccttg ataagagaat tcaaggcgct gacagatata  18780
aacatcatcc agcttatatg taaatccatt aatctcgcgt ttgtctttta gcttaccatt  18840
gaattccaga agatgtaaag atacaaagtc ggattcggct gctgtaagat tagggaatat  18900
cgattgcata atctttctta atgcaacata aggattaggt tcgtttttaa tcagattgtg  18960
atgcttgagt ccaagcttgg gcacatgaat ctctttatca cccagctgta ttttcttcgt  19020
cggcagaatc agttttaagt tcatttttaa ccttcggtgg ttcttcaact tcgataggct  19080
taccattggt aaacatatag aggtttgtaa ttgatgtatt gttactcact tcatgaataa  19140
cttcgtctac gtaaaaatca tatttgaatt ggttcttcgg gtcatagaaa tttatcttat  19200
cacccggggt taattcaaag ttcccgtatg ttttgcagtg cgcgtaacca tcatattgag  19260
acatggttat taatcgttgt gcttcctcga aaccatttcg gtatgtgtaa tctgcatagc  19320
ccccggaacg agataccaga atgctgtttt gtccttcccc aaaagttatt ctggttgcgt  19380
tcttatcaag gaatgaatgc gcgtacacgg ttgcgttttc atatggtttt cttgtatgtt  19440
ggtttgcttt tgttaaccat tcaaaatcga aggctaacgg agtctcgagg ttttgtacaa  19500
actgaccaac caatcgaggt tcacccacca caaaattaat cggctcttgt gtggttaacc  19560
attcataatc ctgaatactt atgccatcga tatcttccca tacaaataca aatttatcag  19620
actcaaccgc aagacctact tcccttatga attccatata ttggttcatc gaatcacacc  19680
atggaacatt aggagcataa acgtttatgc cgtttatcgg aggagcaagt aatggtcggt  19740
cctgataaat taccccggtc atttctacta atgtttcttg tacactcggg taaaacatac  19800
gactaaattt caggtcttca atttcgtgaa taggcgccag ttgaattgta attatgttat  19860
cacccttttga atccacagaa actgcaaagt gtttgcttcc atatattctg gattgagttc  19920
ggtcagagtt ggcattctta acggagacct gaataatttg ttcaccgttc atttttgtat  19980
gtaagttctt tgtgtcgtag aattgcaaca gaccttcatt tcttccgtaa agagaatcac  20040
gcatggtcat agttgtaaat gtcgcagcca gttctacaaa acggtgttcg agccaggcat  20100
cataatcttc gtaaaggcgt atgctgatat taggaaagcc ttcacgctgc atagatttag  20160
ctgtcatttc ttcaagtcct tctcaactaa cgataaagca atacctcgtt cgatgggaat  20220
catatgcatg atgctatcga gcgtatattg gttctttacc agcaagtggt taatttgata  20280
aaatacaaag acttcatccg ggttaaggat aagcttaaag acatcaatca agtctgtata  20340
ttcggttttg tgtttttcgc agcaaccata tgtaaatgga atataaactg aatgcatttt  20400
cttaaggagc tcttcgagac tctctatatc aattgcatca ataacctgca tcttcgtttc  20460
ttcaggaagg tcttcccaat tgtacttttg ttctgagtct tcgacagtct ggatggtgtt  20520
tagaacaagc tccgacttat ctttatattc cacttcaggg aacttaaatt gtatttttat  20580
ccctgcagtt tccattgtcg gatttatcaa tggaccttga ctcatattaa acaaagtctg  20640
ctttgtcttt ttacattttt gacattcgaa cgctaccggg acttttgtct taccgataga  20700
ggaagtgaat accttcagga atatataagg tctccatgct ttcggatact ctccaaaata  20760
atcttccaac agttcgtcta ataattgttt ttgttcttcg acggatttgt tgttcatgtc  20820
gttccgcaca agcagtaaat cacggtaatc agcgactgta aacggtttga aacgatgaac  20880
tccgtctggc atttcacatc ttacgatatt ggccatagaa tcccctttta tctttattga  20940
```

```
tatttataaa tacagtaaag gagcaaatta tgacttatga atttattgtc caaattaaaa  21000
ataaaactat aaattgtagg gcttttacct tgcgcgaata caaagatttg cttcaggcaa  21060
aattagaaaa gcgtatggaa cctgcaataa ttgaactgct taataaatgc actgatgcta  21120
aagggttaaa caaacaggaa gctgaactgc ttcttattaa tctctgggca aatagtctcg  21180
gagctgttaa tgtcgagcat acatgggtat gcgagtgtgg aaaggaacaa gatattcctg  21240
tgactataag tcgcgcaagc atcgtggatg agtctgaagt tattcgtgat ttcggggcgt  21300
ttaaaattaa attccgttat cctggactgt ttgaagatgg cgataaagga aaaatgattg  21360
cttgttgtat cgaatatatt atcacggaag gcggcgagcg catcgttgtt gatgacttaa  21420
atgaagccga aatcgaggac ctgtacaatg caattaccct cgatgatata aatgcactaa  21480
cggaagaact tctcaagcca caggtccaaa tggctattcc tatctcttgc gagtgtggag  21540
cgcattctgt ccatgtaatt aaggggctta aagaattctt taagtttatg taaatgaata  21600
taaacaaaat gtatagcgat gtatctcctg acttgtcaat gagttgggat aaagacgttg  21660
ctaaagtaac tggcgcaagg tccgttaaga acagccttct gggaataatc accacaagaa  21720
aagggtcaag gccttttatg cctgaatttg gatgtgatat aagtaatcag ctttttgaga  21780
atatcactcc attaatcaca gataccatta aacgcaacat cgtctccgcg gtgcggaact  21840
tcgaaccgag gataagcaat ctacaggttg cagttgtccc tatgtatgat gataactcca  21900
ttatcgtaac ggttcagttc agcattgttg atgaccctga taccctcgaa caaatcagga  21960
ttcagctaag tcaaaacggt taatgcttta attttatggc tgtataatgg ttctagaccc  22020
ttacattgga tacattatga aaacagagat tgaatataag ttggaagtat ttcaggacga  22080
gttagatgca gatttaaaaa ttgatggtac acaacttcaa tatgaaacac aaaacaacgt  22140
tttgttgcat agcaaatggt tgagattgta tactaactgc aagaaagaaa taatgcgtct  22200
tgagattcag aagaaaactg cactgaaaaa acgactagac cattatacag gaaggggtga  22260
cccaggggaa gaagtatgca tggatgtata cgagaagtca gaattgaaaa cagtcatggc  22320
cgcggattca agcgtgctga agattgatac ttcaattcaa tattgggcac tactccagga  22380
cttctgtagc gctgcattag atggtgttaa gtcacgaagt ttcgcactta aacatatgtt  22440
agaaataaga caattcgagg caggtaaatg atgaaacaga atattagtaa gattctcgac  22500
gagatggtta tctctgcaaa ctgaataact gaaattgtta atgagatgaa agctcgtgct  22560
gctattatga agagtactaa atagatatgt aagtttaact gaggagacaa tcatgtcaga  22620
taagatttgt gttgtctgta aaactccaat cgattctgcg ttggttgtgg atacagacca  22680
aggtccggtg catccgggcg cttgttataa ttatgttcag agtttgccag ttacggaaaa  22740
tacagaagag caactgaacg agacccaact tttaatttag ctagtgttgt taaccatttt  22800
ggttttgccc cttccttttg gttggggcct ttttatttag aaatcttcgt cttcttcatc  22860
gtccatatcc tcaagctcgg cacgtttacc ggcaagagcg tcacgaacac tgatatcatc  22920
ggaatctttc aattcagctt ctttgctgcg ctttttataa taaccttcca gctccttcag  22980
accgtccatg gtctgacaag aacctatctt agacatgaag ctttcaattg ccgcttcata  23040
cataatttct tcaaatgact tcattatatt tccacctgtt taatgatata attgaatttt  23100
tcgtctgcat accgctgaat acgttctaat gcgtgtttca gtgcaaagtt aatatgaaca  23160
tatttctttt tagcgtttgc tgatttgggt ttgaccccca tatcatccac gatgtcccac  23220
acgtttgcgg tcgatttgga ttcatgtttt cgaagtacac gaccaattgt ctggagtaca  23280
attacctttg acttgaccgg gtgagcgaaa ataatatgat ggaggttttt aacggaaatc  23340
```

```
cccgttgaga atacaccgta tgaagctaca acaataattc cctttccatt ctctgccatg  23400
accttcagag cattacgggt ttcggtatca acttccccgg aaacataata cacattctca  23460
tgaccggctt ccttaagcat ttcaaacatc gatttaccgt gctcgatatt cttaaacatc  23520
aaaaagacgt tttcatcttt tttagcaagc ttaagtgcaa ggtttgttac ccatttattt  23580
ctacgcgtag ctttcgtaat taccttgatt tcatcctgat aagttttacc tttcatttta  23640
acggtgaatt catcaggata tcgaaggaaa atactattta tcttaaggtc agtaacttgt  23700
ccttcatcca ttaattggga tgtggatact ggtttaaaga tatcaccaaa cagacccata  23760
tattgcataa ggtttgcttt gccgtcacgg agagaaccag agagaccaaa tttaaacata  23820
caattagtca ggccttcgat aacggtcgaa atggatttac cagtagccat atggcattca  23880
tcattcataa actgaccgaa ctgtgaaaac cattctttag gttgttttac tgccgtctga  23940
taagtagaca cataaatcat tgcatccgaa tcacgtttag ttccggaacg gataccgaga  24000
caagcttctc gagggaacaa tctataatca acaaagtcat taatcatctg gtcaacgagc  24060
gcagttgtag gtacaaggat aagaaccttg ccttcatagt tctcgagata atatcgcgcc  24120
agaagcgcct ggatgaggct tttacctgca gatgtaggta agttcaatat ttttcttctg  24180
ttgaccagac cgtcgtatac ggcgtctgtt tggtaccaat ggggagtaat cttggtatgg  24240
cctgaataga tttcttttga ctcgacccat ttgtcgaatt cttcgcgaga gatttcttct  24300
ttctcggtga tttgcgggtc aatccaaaat gaataaccaa actggtcagc gaatttttta  24360
atctggttaa ctaagccgta cggtaattta cggttataat ccaggagacg gatacgtccg  24420
tcccaaactc ccgctttgaa tttagggtta aaccgatagt tttcggcttc aaaactgaaa  24480
tagtcacgga gttcatagaa gatgctatct tcacattcaa catgtacatg actaaaattt  24540
aaaaagttga ttttgatatc catgatgatt ccaaggtaat aaatatatct atatttatac  24600
aataaccgag gttcattatg attgataaga actatattga ggaaattcgt gtcctcgaga  24660
aaaaagaagc caaagaaaaa ttagccaaat atgcagcatc acttggtgtt gatgttaaga  24720
aaacaaaaac ctttgataat atgttgactg acctggaagc aggacttaaa gcatttgctg  24780
acatgcctat gcctgatgat aatgaaggcc tgagcatcac tgaccttatc gatgccgatg  24840
atgaattgtc aggtgctaaa tttgatggcg atgagtcagc taaagaagaa gctaaactct  24900
tatttgatgc tccaaccgaa gcaaaggttg aagttgttga aatcgaagaa ccaacagttg  24960
ttgtggttga agaagacgtt ccttttgtcg aagaaaagtt cgaagctgct gttgctaagg  25020
ttatcgaatc tgaaaaacct gtatttgctc tgccaaaaaa ctttagtcca aatcttatgc  25080
ttattggcaa gaaccctgga ttctgtactg ttccatggtg gatttatcag tggattgccg  25140
agactccaga ttggaaagaa cgtccaactg ctttcccaca tcccaccgcg caccaaactc  25200
tatttagttt gatttattac atcaatcgta atgggtctgt tctagtacga gaaactcgta  25260
actcatcttt tgtcacttta aaataagggt ttattatggc ttataccgta actattgctc  25320
ctttggcggc tacggccgtt attggagcaa caaccaattt cactgcgacc ggttccggtg  25380
ctgcagctga aggtaccgaa tcatttgtct ggaccgttga tggcgttcct caatcttctg  25440
tgactgctgc aatggattat gttgctgttg gtccagcagg cagtaagact attaaagttg  25500
ttgcaacaac tacaccagcg gacggcggac cagaaacagc tgaagccgaa acaactttaa  25560
ctatccagaa taaaacaatg tctggtgttt ctgtgacatt aaccccagct tcgattaatg  25620
ttccggaaga caccatagct tcatttaaag cagatgtagt tggcgcaccg agtggagcta  25680
```

```
cttttgccta ttcttggaag aaagacggtt ctcctgtagt tggcaccacg gatactttag  25740

caatcgatac aagcgccgaa ggttcccagt taattgaagt ttctgttgtt gtatctgcta  25800

cagattataa tcctgttaca gttaccaaaa ccggtaatgt aactatcaca gccaaagtcg  25860

cgccagttcc agagggtgaa ctaccttacg ttcatccgct gccagttcgt aattcagctt  25920

atatctggtg tggttggtgg gttatggacg aaattcagaa aatgactctt gctgggcaag  25980

actggaaaac tgatgctcca gatagcccgt attatttgca ccgatatacc cttcaaaaaa  26040

tgattaccga ctatccagag gttgatgtac aggaatctcg taatggtcga attattcatc  26100

gcaccgcttt agaagctggt attatatacg attacgttta ttaattaaaa agggaccttc  26160

gggtcccttt gtttttatgg tactgtacaa acgttgcctg gcataaaaac cctgtttaca  26220

agttaaaaat tccatgttaa gatagcttca ctaactcaac atgagaatca ttatggataa  26280

ggttaaagta cattttctgc atgaatctgg tatgacattt attgaaatcg ccaaggtatt  26340

aggcgggact gctaaagaga tggcaaaagc ctgggttgat gtagaacaag ctaaagctaa  26400

atttaaagcg aaagaaaaga ttgtttatcg taaacgtttg aataacaaaa aggtgaagaa  26460

atgacatttg cagaagaact acgccaaata gccaaagagt cacaagataa agttgcaaat  26520

gactttattg ctatatttcg caaagtggct attgccgctg ccgagaatgg caaagatgct  26580

gttaatatgg cagtttctga aaaagagtat gaagaaggaa accgtgcaaa gatatctgaa  26640

tttctgcggg cagaaaaatt tacatcattt acctggaatt atgactggca agaagccaag  26700

cccatgctgt atgtaaaatt ctgacccttt ttgcttcaaa taaaaatgcg gtataatggt  26760

tctagaccct ttgtgactat taattccttt cagagaaaga aagtatagtg ggtctaattt  26820

ataatgatat ttataacatc aaagtgagag attatgttta aaaaatacaa cagccttgaa  26880

aatcactata acaacaagtt cattgaaaag attcgtctac aaggcttcac cagcggtgaa  26940

tgggtagctc gtgaaaagat tcatggtacc aatttttcat taattattga acaagacaat  27000

gtgacatgcg cgaaacgcac tggacctatc ctacccgcag aagatttcta tggttatgaa  27060

attgtattaa agaactacgc agattctatt aaatctgtgc agaaactttt gcaggatatt  27120

aattaccagg cttaccagat ttatggcgag tttgccgggg caggtatcca gaagaatgtg  27180

gattacggtg ataaagattt ctatgtgttt gatatccgcg ttactaagga agatggctct  27240

gaatccgtcc tgactgacac acttatggaa gccttctgca ttattcataa gtttaaagtt  27300

gctccgcgcc tggctaccgg aagctttgaa gaccttatta aactccctaa tgacctggat  27360

tctgtggtcc ctgattacaa ttttacagtg gataacgcag gattgactac agcaaatacc  27420

actgattttg atgcaaaggt ggaaggtaaa gtattcactg ctgaaggatt tgtattaaaa  27480

cctgatgttc ctgcctggtt acctaacggc gagcgtgtag cgattaaatg taagaactct  27540

aaattcagtg aaaagaaaaa gtctgataaa cctattaagg ctgctgttgt gttgtcccag  27600

gaagacctgg atattttatg gaagttcact gattatgtga ctgttaaccg tattaataat  27660

gttatcagta agattggtga agtatctccg aaagactttg gaaaggtaat gggtttgact  27720

gtccaggata tcctggaaga agctggtcgt gaaggccttg aattgaccca gtcagaaaat  27780

cctgttgaag ttaaaaagca acttatcaca aatgtaagag aaacattaag acatgtttgg  27840

attgcattaa ttagtgaata aaaaaagggc cgcaaggccc ttattctttt tccagtggtg  27900

gaagtttaac accaagataa gaactcaatt ggctttggtt agccatctta tccatatcag  27960

ccccatcaat aaggcgggct tctttatcat ctttagcaac ggtgtagggg ttagctgtca  28020

aagcataacg agctaacagt gcaaccgtag gctgtaagct ttcagggtca acaataacct  28080
```

```
tgaattcccc aaccgatgta tcaccctcat catcaacttc gctaagccct tccgtataag  28140

gcgcataata caaagatgcg accgtctgac cctcgcccat atccgcattt acgccaacaa  28200

taacataatc gcatggacta ttcatatctg cataaagagg caaaccgttc ttcagaacac  28260

cataggccaa ttcatcctgg tcttcctttt tctcaaccca gccagaagcg gctaaaatag  28320

ctgcacaacg ggaagaagca accgcatatg taccagcaaa cgaagtctga cgttgaactg  28380

cagaattcat ttcacacata taataataca gggttcgtgc gcggtcctgt gcgttatcat  28440

atttcgggtc agtgagattc aacacacctt tttcagaaac accttgtacc ttgaagcgag  28500

aactaacagt aataagggat tgcaatacat ccttattaat ttcctctgcc atttgaatgc  28560

cgagaatatt atcgatgaag tctgttgcat cgaaaccgtt tgcttccagg tcctgagcaa  28620

gctcgacagt taaagaagtt ttcaactttc tggatttaac ttcagtctgc catttatcga  28680

tacggaaacc agcttcagca atttcaggat gcccctttc aaatttatca gtgaaagcag  28740

catctgacat cattcttata tgtccagcag caatggcttc agaaataact tcacctaaat  28800

cagtttcgag tgtcccggca aagggggaag cttccagaac tttgaataca acgctttcaa  28860

actgaaacat atcgccgact gcataagctt cgtctttgtt cgtaaattct gggatattct  28920

tacgctcgaa cataccaatc tggcccgcga atgtcgctcc accaagatat gtcattttat  28980

catctggggt cagaacacga acaccataca acgctgcaac aggctgggta gttttctgtt  29040

cggcaacgag tgctttaaaa attcgtttat tcgtggcctg ggtataagaa agcaaattag  29100

gacgggcgac ctggttggcc gccgttaatg ttgattcgtg aattagtgcg ttaatctttt  29160

gcatttacgc ctcataaatg attggcggaa gtttaacacc gagcagataa gacatattgc  29220

tctggccggc cattaaatcc atattagttg catcgataat acgagcttct ttgtcgtctt  29280

tagcaacggt gtaagggtta gctgaaagtg catatcgaac catcagggag atagatggct  29340

gcaaactgtc tgggtccaca atgaccttaa acgcacctac gtgttcttca tcatctaagt  29400

ccaggccttc ggtataagga gcatagaaga ttgagcctac gacttcgttt ccaccgtaat  29460

tttctttaac gccaacggtt acataatcca atggactgtt aacatcacag aatacaggaa  29520

gaccattaat caaataaccg tacgctgttt caggaagcca ttgctcgtct tcaggtttat  29580

gcttcagcca gccagaacca gccaacatag cagcaacacg gctagaggca acaacaaagg  29640

taccggaata agatgtagtt ttctgaattt cggagttcat ttcgcaaacc agttcgtaca  29700

gtttacgtgc accttctgga gctgcatcat atgttaaatc gatggtgcca ttgtcagaaa  29760

cgccagttac tttataacgc ttggaaacgg taataagaga ctgaagaaca tctttgttaa  29820

tttcatctgc cataatagtg gcaagcaggt cttccaagaa agcaggagcg ttaaacccat  29880

ttgcttccat atcctgagca agttcaacag ttagtgcagt tttcaattta cgtgttttaa  29940

ccggagcatt ccatttatta acctggaata cagcattact aatctcaaca tcaccggctt  30000

caaatttctc ggtgtgtgcc gcatcaggaa ccaaacgaat ggttaatgca ataagacctt  30060

cttgcagaac atcagataac actgtttctt tggtcgatgc aaatggatta tcaaccagag  30120

ctttataaac ggtattttga tattttacat attcaccttt agctacaggc tgagtggctg  30180

tagttaattc tggaatagtt gtacggtctt tagaaccgac ttcgccacca taagtagcac  30240

cagtctggaa actgaattca ttatcaggag taagatattt aacaccgtac agagccgcaa  30300

ctggctggtt agtacgttgt tcagcgataa tatcgcggta aatcaatttg gttgtagcac  30360

gggtcaaagc aacaagattc gggcggccca aggagttgct ggtagtggta gttgactcgc  30420
```

-continued

```
gcagtaattt gttaatcttt gccatttgcg ctttcctttt gtgatatact ttatttataa  30480
aagttgttta caacccgatt aagataagac ataatgattt catactgagt taccaaacaa  30540
tggagtctaa aatgaacaaa gtatctttcc ttcggaatac ctttaaaaat ctggaaattg  30600
aagttgttgc attggtcaac aaatacccaa atggtgttaa tggtaatgct ctgaacaaac  30660
tagttaaaaa atatgaaaac ttagcatatg atactgattt ttggtggaat ggtaattatt  30720
ctactcacac caaagacaaa tcaggtaact ggttgaaact tcaagagaac agtgttaatt  30780
tcagagacct catcaagcgc cgggtagaag ttcatttaaa tggtatggta tgaaaacaag  30840
aaagggacct caagggtccc tttttattta acttaatcta agattaaatt cccttaacat  30900
atacacgtct aaagtaaccg ttcaagccga ggctgttaac gatgtccggc ataccgtttt  30960
gaatacgctt ggtcggagcc tgagctgccg ggtcagcgaa cgggttaata ccgataccgt  31020
aacgggtttt gaagcccata accggctgga agtttttcgg gtcagagcca cgcagcgggg  31080
tcagtgcaac atatggtgcg tagtagatac cagcatccat ttcgttagcg cctttgtaac  31140
cgatggtgaa gtaatctgcg cgagcatact ggtcgatgta gacacggtat ttgccaccca  31200
gaacaccagc gaacacagct ttagtggtgt caacgttgaa acctttaccc agaccctgag  31260
cagcataaga tacggaggta tcaactgcag ccagtacgtt aactacgtta cgggaagcga  31320
tgatgaagtt acctgcacca cgaccggtct gacgagcgat ttcagcggct tctttatcaa  31380
tctggaacag taaagctttg aagctttcac cagcccaacg agcaccacgg atatcaatcg  31440
ggtcctggaa gtcaaacaca ccagctttag cgccaacggt gttggtcata ccagatttac  31500
caacctgagc ggagtagtta atccaatcga taacttcacg gttgatttcc agcataattt  31560
cggtagccag aataccactc aattcggcat cagcatccat accatgaaca gcgcgcaggt  31620
cctgtgccag ttcgatggag tagcttgctt tcagctgacg ggatttagct tcgataactt  31680
gtttatcgat acggaagccc atttcgttcc acgggttatc agtagaaccg ttaaagcctt  31740
cctgcaattc ggcgatagaa gtagccatac cttcagcgat ttctgccaac ttaccagctt  31800
cgagcagttt ggtaacttca gcgtcaagtt tagcagcatc agtagcacca gcatcaacgg  31860
ttacagcttc aacagcctgg tagtgtgcag aaccggttgc ttcgaagaag tgagaataaa  31920
ttttaccaac agtaagcagt ttgcctgcag ccagtgcttc gaaagtttta gcagcgccct  31980
gaccagagaa catagcgttc ggagcataca tcgggtggaa agcttcttta gcaccagatg  32040
caacagggtc tttaccgtaa actgcacgca gggcaaatac ctggccagtt gggttgttca  32100
gaggctgtac gccacaaata tcaaacgcaa tcagatgcgg gatagcacga cgaaccatac  32160
ccataactgc cggcccaatc tgagttactg caccagaggt ctggccagca gcgatattgg  32220
tagcatcata accatggtca ccaccgattt cagcttcagt caggaaagaa ccaaatgctt  32280
cggagatttt ttcgtcacgg tattcaggag cggtcaggat atcttgttcc tggttttcaa  32340
agattttagc gatgatagct tgtttagaag caccaacgat ttcaggaaga gcttcgtttt  32400
ccagcagagc ggaccatttt tgaactaatg cattcttttt catgtgttgt ataaccttat  32460
taaattaaga aattcgtgat gctgcgagag cagacaagtc cgcgaaggac agggtaggct  32520
tggcgccttt ttcttcaact gcttctgaga tgtaattcag tgccgcagca tcgtctacag  32580
aattatttat agctgcttcg gtgataggtt tttcggcggt gtctacctga cctttaacca  32640
tttcaacgat agcgccaatt ttggtaccga acgcatcgga ataatccata ccttctacca  32700
gagaaccaac tttttctttc tgagattcgg tcaggtcttt ggtcgcttca gtcaacgcaa  32760
cttcacgttg gacataattg atataagcat cacgcttagc aacttcttcg aacagattag  32820
```

```
cggtttcttc tttctgttca gccagttctt cctgcatttc tgcaacaaca tcaacagatt  32880
cttctggaac aacaacgttg tgctcaacga acagttcttt catgccagta aacatggatt  32940
cgaacaggtc agctttaatg ccacggtcga cagccagttt gttttcagca agccattctt  33000
tagcaacgtg gtccaggaat ttagctgcag attctttcag ttttttctct gctttttcgt  33060
cggattcttc tttattcttt tcgacttctt cttcagcttt ttcagcaatt ttctgaatgt  33120
gagattctgc cagtttgatg gcgtgttgct tgacggtagc ttcgaataca gtgccgaagg  33180
tagctttcgc ttccggggac aaattaactg attcgaaaat actatcgaga gcaacggaag  33240
catcgatgtt ttgagcttca gaaatgagtt gttctttaag cattttgtag tcctgttgtt  33300
aagatataca tttatttata acgtctttaa agcctctgcg agagccataa aggcgtcatc  33360
ggcactggta tcggcttccg ccgtttgtga ttctgtaatc tgctttggtt tgacccaagc  33420
gtccggagca cttggccccc atactgcgtc tactccaacc gtcaatttaa aaccttcatt  33480
aacgatgcta taacctttg ctgatttagt cagggaacca agtccacgac tagatacgcc  33540
aggaatccaa cctgctctta tattcgcagc aagtttatca cctggaccat ggtcgccttc  33600
gataatacgc gcgcggccat atacatcatt ccctttccac cacatttcct cgataataat  33660
tgctgcctgc atagggtcaa cgtttgcgcg aggtggatgg tttaattctc caagagactg  33720
cttggtttca acctgttcgg cgatatagtc cgcaacggct ttttccaaaa tatgtttagg  33780
ataaagtcgt ttattacggt taacaacttc agcttgtagg aaaatacctt caatataaag  33840
tcctggcttt aaaccgctgc tggaaccatc atgagattcc aacatcggta caccatcttt  33900
aatttcgccc ggttgacccc agtgttcgat tagtaactct ggtttctgtt ccattaatca  33960
agtccgaatg ctttacgctt agctcgagct tttttgcgct tgcgctctgc tctgatttgc  34020
gtagatgggt ttgctctttt cgttttagta gccagacggg caatttgacg acgtttagct  34080
ttagaaagac cagttgtttg gaaagcatta cgcttacgag tagctcggtc ttttgtgcgg  34140
gttaactcac cgcgagacga tacatgttta acgataaatt cgttaagctg aacaccttca  34200
ttcagagcgc cgataaccgt tgctttttcg tattcaccgg ctgcaaacat gttttctaca  34260
ataatattta tatcgtcttt ttctaaggct tcagataatg aatcaaattg tccctgagct  34320
tcttcggaaa cactttcgat gttttcaaga gttaattcgt aatcatcagg gataataaac  34380
attattcatc gtcctcatca tcatcatcgt cgccttcgtc agcgtcatca gattcttttt  34440
tgtctttctt ttctgcttta ccgtcgtcct tgccttcatc ttcatcttct ttaggctctt  34500
cgccttcaat catgatggaa cgtgcaattt caatcttacg ttcttcaatc aaactaccgc  34560
atactgggcc aatgttttca gcaaaatatt tgcgaacggc tacgaggtcg tttgatttaa  34620
tggcttcaaa taaatcatcc attagaaatc ctcttcttct tcttcagggt tttggaaacg  34680
agcctctttg gactccaatt caatttgctt agcttcttga ttaatttctt catcagacat  34740
ctggaggaaa tccttcatag ccgtttgatg cgaaatatat ttaccgataa acggttcagc  34800
catcgttagc atattgattc tgcgttccat gatttctgca tctttcattt cggtgaaata  34860
gctatcacgg ttgaacgtaa ctttaatatt atttagttcc ttgtcccatt cctcttctga  34920
aataactttt ttcaggataa ggtttgtttt aagcgggtcg aggaaaactt cttcaaattt  34980
attctgtagc tgcctaatcc atttagcgaa attcaattca tcacgagtaa ttgtcgcgcc  35040
tgcatcaaac ataacgccac tgttttggtc attagggata cgagataatg gaattcggag  35100
agcctgatat aggttgttct taaaccaacg aacatcgtcc atatccgaca tgccttgtgc  35160
```

```
acccgggagt gtatcaactt cagtgactgc tttaccatca cgacgttgca accaatagtc  35220

ttctgtcatt gacatgttgt gctgttggtt tttgatttta cccgtggttg catcatatac  35280

gacacggttt ttcatcgtgt tcataatatg ttgcatatgt gctgctgctt tacgagacgg  35340

catattcccg gtatcgatat aaaagactcg gcggtctgga gcacgagtta tacgataaat  35400

gactaaagca tcttctaata gttttaattg gtttgcaggt ttaattgctc gttgcaagta  35460

tccgatgata ttcttgccac aacaatcgag taatccagaa tgcgcatata caatcgccgc  35520

gcgaggaatt tttattttag tacctgcttc atatatacga ccatcggcac aataactttc  35580

atggccagta tcgtatacaa aatattctct gtaaccgtcg acaatttttg taccattttc  35640

catgcgtgta acgatttcac ggatgaactg gatttgtctt gggtcaaggc gac         35693
```

<210> SEQ ID NO 2
<211> LENGTH: 16184
<212> TYPE: DNA
<213> ORGANISM: Artificial Sequence
<220> FEATURE:
<223> OTHER INFORMATION: a part of DNA of novel bacteriophage CJ20 Contig00002

<400> SEQUENCE: 2

```
gttccagtgg tctccaaccc agcgcattgc ttcttgggcg gtctcaatga ccacctgagc     60

aatctcttcg gtacggcaac ctacttggat ttcgtcatgt acccacgcca tgtacgcaaa    120

gtccccatcc caaccatgct tcaagccttt ctctacgagc atctcttcgg tcttgataat    180

ccacagtttg cagattagag caccagcaga ttgcagtagg gtattcaggg cagcgtgagg    240

actacgaacg tgtaccttac gaccatccag acctttaatc cagcggcgtt tccacttgac    300

ttgttgctca ccagctaccc actgagagga ctcgacaagt gtctgttgga tagactcgcg    360

gagtgctgca atcgctgggg tgttctcaag gaatttcttc ttgagttcct taccacgttc    420

tttaccagca cctacaatct gcccagtctt ctcatcgcca gcaccataga ggaacccata    480

gataaacgtc ttagcgttat ctcgcattag gtcgtgttcc ttattatgct tatcacgggc    540

aacgtttggt gctaagtcgg cagcaattgc gttcttccag tgaatgtcac cattgagaat    600

ctcgtgagca tactcaccgt tgtcaaagcg agccatgaag tgtgccaagc atctcagctc    660

caaaccagag gcgtctatac cagcttgaac ccaaggctta cctgtaagtc cgtctaggtg    720

atgttcagcg ccaaaagcag agcggcaccg atcaccataa ggagagcgga caccgggtat    780

ctgtgcgagg ttagggaaag cgtgagtagc gcgcccagta acagcaccat tggggttaac    840

agaaccatga attttaccat cctcagcaac gtaacgaagc catgccttgt ctccctcagc    900

agactgtccg attctcttct gaatcatcaa gtattcttta ataaggtcga tagcggcttg    960

cttctcaggg tcatccactt ttactccctc taggacttca tcgtccacca caggagaacc   1020

tttgtctgtg tacttagtcg ggacccatcc agcctcttga agtttcttct gaatgtggtc   1080

acgggacgaa gggttaaaca ctacgtgctc taccggagta tatggggcac cagcaacgta   1140

ctcacgggta tccagttcac aaggctctcg gccttctcgc tgtgccttgt tcttaggctt   1200

cttaaagata ccaccaactt taggtgtctt aatgcgaggg tatttaggca gtggcttacc   1260

agtcctcgga tggcagaaca tttcggtgcc acctttaggc tgataccacg agccgaacgt   1320

ttcggtcagc ttacgcagca actctgagcg acgagcagct aactctacgt acaactcttc   1380

gattgctttc gtgtcaaacg ggaatccgtt acgctcttgc ttagcgagca gccatgcagc   1440

acgatgttca acgtcaacgg cctcaaggga ttctgaccag aacgtagtgt atcctacgtc   1500
```

-continued

```
cgtaaagtca atctcaggag ggaagtaatg tttgtcagag agtagcttct caaggagagc   1560
tttagtgacc acaacgtcct gaacgttata gtccatcatc tcttcgttga agttccacca   1620
ctccattcct tcaacgtatt cttcaccctg ctcttcaagc atacgcttaa agtcgtcttt   1680
gtattcaccc ttcatctcgc ctaagcgata accccacgcc tccaaagcgt gagacccaaa   1740
gcgtttaccg ggcaacttac cggaacgcag aagacccata tcggtgtctt tcaggttaga   1800
gtgaatcaag cgtgacaaca caagtgtgtc aatacagttc tcacggggta ggtggaactc   1860
acggttaagc tgtaacttag ccagtttggt caatgcggga acgtcatact tgtgaccgtt   1920
gtggaacaca ataagaccgc ctcgtgcaac ctcggcttcc agcgcatcca gatacgcacc   1980
gaagtcactc ggtcggtagc ttacgtactc atcggtggag tagtcgtaga taaccccgca   2040
gtggaactta gtgacgctct ctaagagggc gttagcttcg atgtcagaaa cgatcatatt   2100
gatttctcct attgattatc gtgacttaac aatctcttca tacgaaacaa ctgtcaagaa   2160
gcctgtgtta atcgggatga tcttatcagt aacgattgca cctcgtggag ttacaccact   2220
aatgtaggac acttgtgcat acttatcact aactgagcga acatacccat atccacaaac   2280
acctcccctg ccaaccttaa cccaatcacc agccttgatg tgggtcatag tgtccttatc   2340
gaacaccttg tggctcagct tggtaacttc tggtttcttc catccagtct gtcgtgtcca   2400
agtccagcct aagttcttca agatgtggac agcggagcga ttcttagctt catgatattt   2460
aacgtcctca agttcagctt ccagtttagc gatttctgct tggataactt tagggtcacg   2520
catgataata tctcctatag tgagtcgaat agtattcatg aaggccacca ctttggcgac   2580
cttgagtata ccactcttag ctatcaatct tgtcgaggat agccatagct tcatctacgc   2640
gaccagcttc atggattgct gtcacggcag ctttggtaag cgcattgacc agacgcagtg   2700
cttgctcatc tgtcaacgtc atacgctgag tgtgattctt agaggactta gagtccttcc   2760
aacggtaaac catagtagcc tttccgttac gaacgttgat gtgaactcgg cggttccatt   2820
ggtcggcggt atcggataga cggatagttt cagctacttg tgacatggta gtttctcctg   2880
tttaattact caaagaattt ggaaagttgt tgagcttgat tagctacacg agctgcctcg   2940
gtaactttat tggatgcact gtcagccagt tcgtttgagc ggatagccag agcacgggac   3000
tgtgtggcct cattacgggc ctcgtcgttc aggcgcttag cttctacgtt gtacaaacga   3060
accagcagtt tgccaaactt cttaatcaat ttgaacatgg tatgtgtctc ctttagtgag   3120
tcgtattaaa atcatcaaga atcctgtcag aagtcagtgt cgtttgacca gtctgttgac   3180
tccgagtgtg actcttcttc ccctgtgtaa ctcgacggtt cgagccaccc tgtttccttg   3240
ttgtactcca tgtagccagc aataccagta tcgccagtaa agcggcactt gagaatacga   3300
acgaggacaa ggttaggcat atcaccttgc tggttacgct caagggcaat aatagtatca   3360
gatagttggc gaagtgcgcc agaaccacgt aggtcagtaa tagaaacagg acgaccttcc   3420
tcatgtgctt tacctttgtc tgggttctta aggtgacata taacgaccag caccacacca   3480
gttgacttag cgaacccttt gagcttggtc atcaggttgt caatcatctt gcgctcatcg   3540
gattcaccag aagcggacac tacgattgag atgtggtcaa ggataattac gtcgcaacct   3600
aagcctgagc gcatataggc cagcttagcg agaagcctat cggtctcagc ctcagcgaat   3660
gagtcataaa gatggaacgt gtcgttaccg aatagttcat cgaaccattg gtcgaactta   3720
ccgttctcaa tgatctctct ctttagtgag tcggattgac gcaggcgtac atggttgtgc   3780
agacctataa ggtcctcagc ggtttcctca acggactcct caagcatcgc caagcctacc   3840
ttcttgccca tcgctgtgcc ccattgtaga gcttgctgac gaacgaacgt tgacttaccc   3900
```

```
ataccggagc cggaagttac cataatgact tcaccaccac gggcaccaag tgtcttatcg   3960
ttgataccac tacagccact gaaaagtaga cctacggatt cctctgacga taagtgttca   4020
cggattcgtt ctcgtaacga aagagccgat accactccat caggaatcca cgggccagca   4080
ttccagactt gctccatgat ttcacggtcg tgaccattaa ggtgacactc attggcatcc   4140
ttacacggaa ggactgccac tcgtacctta ccagcaggta gaacctgtgc ggcctcttcg   4200
actgccttgc gtccagcttc gtccatgtcg aacatcaaga taatctgttc gaactggtca   4260
aagtattcgt agttggcagc gcatgtcttc ttagcggcag gggcaccgtg acccaacgac   4320
actacaggat acttgcagtc ttgaagttcc atcacggtaa gcatgtcgat ttcaccttct   4380
gtgacaacaa tcttcttacc gccattccac aagtgcttcc cgaacagggc atcactcttg   4440
tgactaccag ttgtcttaaa gttcttatct ttatcgcgaa ccttctggct cacaatgttg   4500
ccgttctggt cacgatagtc agccacttgg tacatcacac cgtctacttt ggcaatccag   4560
tagccagcct tctgacaggt ttccttagag atgccacggg cagttaacgc ggagtaacgc   4620
ccattggatt ccccaaagtt ccatacgttg taagtcattg gtttacctcc accgactata   4680
cgtcttcttg atgatagctc ctgtttacgt tcttctgagg ctggaaccct gtgctcacat   4740
acaaagcaaa attgatggcc gtcagaatac acagagttac catcagaaga cccacagttc   4800
tcgcaaggag cgtgatatag gaaaatacta tcttgctcta attccatatg gttattcctt   4860
aatcaacatt gcgaacaaag ggaaaccgtt gtggtctccc tttagtgagt tcagttaatt   4920
atccacggtc agaagtgacc agttggttag tttcccacca acgcttaagg tcgaacgatg   4980
ggcaagcctt cggtgctaca tcgtgatgtg cgcgaagaac agcgccttta tacttagcca   5040
gtagtgtgac aagcagtgag cggagggatt gcatttgggc tggcgtaaag ttagcatcga   5100
acttaccttt atcgtcaatg ccacctacaa ggcagacacc aatagagttg tggttgtgac   5160
ccttagcgtg ggaacctata gccatctcgt ctcgaccttc ctccacagta ccatcgcgtt   5220
tgatgataaa gtgatatccc acatccagcc agccctgctc tttatgccac tggcgaatct   5280
cacggacacc tacgttctgg ttaggtttag tcgctgagca gtgaacaaag attgcgtcag   5340
tagattcacg ttgtttaaac tgtacacgag ccattatttc tttcctccct tcgattgttt   5400
cagcttgtca aatggcacct cctttttggg ttctttgagc cattccacag gaattaattt   5460
gtcagcaaac agaataccgt gcttctcaca ccattcgccg taactggtcg gagacccttt   5520
atacagcttg gtacgtgagc ttgaaaatac cagacggatg tccagttcgg gaaactgttc   5580
gcgaatcagt aagtgtttct ttcggtcgtc actctcccat aaacctttgg tttcaataaa   5640
gattccgtta ggcagcagga agtctggagt gtagacatgg ttactcgcag ggacaacgta   5700
agggattttc cacagttcat agtagaactt aatgccctta ccctctagct gcttagagac   5760
cttatcttct aggccggaac ggaatgtccc gacctttctg ataccacgcg cagcgtatgc   5820
gccagccact tagaagtctc cgtcttcgtc ttcttcgtag gactcactgt cgtcttcgtc   5880
ccagctttct tcgtcgcgtg gtttgctcgc tttggtagaa ccagaggcaa catagccgtt   5940
ctcttcaact tcgtcagccc aatcgtcttc gccgccacca aaggaagcca gttcgacaag   6000
cattacggat tccagttgca gcttaacgct tgcacctaca gcggtgttcc acttgtacgg   6060
aaccagagag tacttgactt tcagcttaga gccaccaccg ataatcggta cgtcttccat   6120
cttcttgccc ttggagtcaa ccacaaccag attgatgtgc ttggtctctt tggtcttctt   6180
gtcttggaaa gacgcgtagc atttgaactt aaaggtagtc gtaccgtcac cgttatcgaa   6240
```

```
gaacggcatg tcgccctcat acggtttcag cggtttctta ccacgagcta cggctggcgg   6300
gttggcctca tattcctcaa cggcagcagc ataagcctct tcgtgacact tcacgatttc   6360
atcgaccata cgttgacaac gagggtcttt gttaggaatg gtcaggtcaa ctttatatac   6420
accacgaggg ttcccaaagc cacgctcttc gttgccgtag tctggcttgg cgatgtaagc   6480
gtaaggttca gcaataccca gcgcagaggt gaaaatcttc ttagccataa tgttaatctc   6540
ctttcggttt cgtttagttt ctcagaggga gtcttctccc aatagtgagt cgtattactt   6600
cggtgctaca catggacgca cacgagtaac ctcaaagcca gccggaacgt attgccattc   6660
ggctaactcc agagcttcgt ctagggtctc agcgtagatt ggcacctcaa aggaatgctc   6720
agaggactct acggtagccc aaaacttctt attgtccaca ctaagtgaac ctgtatttac   6780
gtttgacata tcagtaacct ctcgatagcc attggttgta aagttccatg tagtgaccag   6840
cagattcctc gtcaccacgt tctatacatt ctgtccacat tctgtggcac cattcacttg   6900
gcttttccat attccacctc tatggcccaa tacattaagc gaagtaacgc tcccactcca   6960
gcgcaaatta atccgaagta cagaacatcg ttaagcgtca tagcacttat ccttatgttt   7020
ctcgtacagt tcaccataga atccagcttt cgccatgtct ttctctaagt aagccagttc   7080
ggacttctta ccagcacgta gtctgtactt taagatgttc ccgaagcaat aacctttgaa   7140
ctgctcacga gtcattgaac gagcaatcac ttcgatagcc tcaatgtcgt caaacagcat   7200
gtagtgggaa ggcttagtga caccctcgat tggtttagct acaggttgac acgtatgtgg   7260
ataacggtca tctttctcta agcacgctat gcacaccatc agaacacctc cttgattcgt   7320
ttgagtaaca gacggacgaa cgggaagcgg gtcactacca cactaagaac cggacgtttc   7380
ttgtctattg ctttttcaaa gtcaccacgg gtgataatga tgtggacgct tggtgccaaa   7440
ggaactgtgt caccaataag aggtaactta gctcggcgct cgctcgcaca tatgattgaa   7500
cggtcagcac ggcgaatcgt gaaattctta atgctcttgt tgtaatgaag tcgaaacata   7560
tagtgtctcc tttagtgagt cgtattaagc gtgaccatct ggcatatcgt catcgtcgct   7620
acagtgtagc gcaaggcatc ctatgatgat aattagcaat ggcattacgt acatcatgat   7680
gtgtacctcc tttagtgagt cgtattaaac gcagaaaggc ccaccataag gtgagccagt   7740
gtggttacat ttctcttgga gggttgtcct cggtgccacg gaacattacg aacgatgggt   7800
gacgcagaga gccgtcaggt gtttcctcca tgtacgcaat ctggcaagcg tgcccgttgt   7860
agtaggtttc accttcaatg ttaactgtgt tggtaaattc atccattaag gtgcgagaga   7920
tgtttgtggc gttaactaca cgaccactct caagaagcac ctcaaatccg attactttac   7980
cttcattcgc taaaccttcg gttccccaca caagaccctg aatgatacca tcagcctcgt   8040
tctctggctt gagtttccac cagccggact tcttaccgcg cttatagata cacatcgggt   8100
ctttcacgat gagaccctca tgcccttctt ctcgcttctt ctcgtacagt tgctgtagct   8160
ccaccatgtc gtagacctcg taagactcag ccgcttgcca ttcaatttca gggaagtatt   8220
cctgtagcag aggcagcatg ttcttaacgt gttcctgcat gagcaacgtc attacatcac   8280
aatcttctcc agactctacg atgtgcagcg ggaggatagc gtacagtttg acgtgaaggt   8340
gtccagtgtg caacttgaat ggaaccttat ctttcttacg gattggttca acgaataact   8400
cttcgtggaa ctcttggttc ttggtgtcgg tccacttggt acgcagtagg ccggaccctg   8460
tgttaaagtc cacgcctttg accatgagtt ccccatcaag cataaatcca tctctgtaga   8520
agcagcggtc atcgctcagt agacgcttcc agcgaacatc aaatccgttt aagtgctcca   8580
gtgccggaat cgttttagat acacgagaga gccagcaact gttagcggta ttgtctacgc   8640
```

```
agatattccc acgtacacca tcgtacttga tgtcagcgat aagataccca gcgttatcca   8700
gagctttctt aatggaagac tctacgaaag acacggcttt aaacgggttt gtcttaatgt   8760
tcatcataat gtttatctcc tattggttaa atgactaagg ccactcaatg agcgacctta   8820
agcattatcc ctatactgag tcgtattact tccagtgctt caaatcgcta tgtaccttgc   8880
gcagccactc agtctgtgca ttacatcgga catcttcgtc tgactgttcg aaactcttgg   8940
ctgtcagtac caagccatta cgcaggacaa ttcgaagagt ctctccagat accaatcggc   9000
gtagtgcgta gttctcatag cgataagtct cagtgaccac atcaacatcg tggtcttctc   9060
tgagtcgctc gatagcatct ttgtatgctg ccagattacc gctgtataaa cgacccatct   9120
tattgaccct cccagcagcg tttatgcgca cgggtgcgta atggcttatt aaacttacga   9180
cctttggttg cctcgaagtc atgagcgtta cggttagaac gtttggtcat cttttcgaag   9240
ttacgcatac ttaaagtcct ctattagtaa ttctttaatt taaatcttta attaacactt   9300
aagggtctta aagttaaacc ttaaggttct cctatagtga gtcgtattaa ccggaagaag   9360
gtcaatcata aaggccactc ttgcgaatgg ccttgagttt gtccctctat agtgagtcgt   9420
attaatttga cgttatgcga acgcgaagtc tgacttaagg atgtcctgta ggttcaagtt   9480
acctttagcc ggaagtgctg gcattttatc caattgagac tcatgcaact ggtcggcgaa   9540
ctgctcatag aagtcagcca gtacatcaca agactcatag gtgtcaacca tagtttcgcg   9600
tacagctttg aacaggttgg cagcgtcagc cggaatggtc ccgaaggagt cgtgaatcag   9660
tgcaaacgat tcgattccgt acttctcatg tgcccacact acagtcttac gcaggtggct   9720
accatcttgg ctatgcacaa agttaggagc tatgccggac tcctgcttgt gagcatcaat   9780
ctcgctatcc ttgtttgtgt taatggtagg ctgtagacgg aactgaccga ggaaaatcag   9840
gttcaagcga gtctggatag gcttcttgta ttcctgccac acagggaatc catcaggagt   9900
tacccaatgt acagcgcaac gcttgcgaag aatctctcca gtcttcttat ctttgacctc   9960
agcagccagc agcttagcag cagacttaag ccagttcata gcttcaaccg cagccaccac  10020
cgtgacgcta acagcttccc aaatcagttt agccatgtaa ccagcagcct gattcggttg  10080
agtgaacatc agacctttac cggaatcaat agctggctga atggtatctt ccagcacttg  10140
ttgacggaag ccgaactctt tggacccgta agccagcgtc atgactgaac gcttagtcac  10200
gctgcgagta acaccgtaag ccagccattg accagccagc gccttagtgc ccagtttgac  10260
tttctcagag atttcgccag tgttctcatc tgtcacggta actacttcgt tgtcggtccc  10320
gtttattacg tcttcttgca gaatcacgtt gactttctta gcgacaatcc cgtagatgtc  10380
ctgaacggta ggactaggca gcaggttaac agccataccg ccaacctcat ccaagagcat  10440
cgctgagaag tgctgaatgc cagagcaaga cccatcgaac gccagcggaa gagagcagtt  10500
gtagcttaat ccgtggtgct gtaccccagc gtactcaaag cagaacgcga ggaagcagaa  10560
cggagaatct tgctcagccc accaagtgtt ttccagtgga gacttggcgc aagccatgat  10620
gttctcgtgg ttgtcctcaa tgaacttgat gcgctcaggg aacggaacct tatcgacacc  10680
agcgcagttt gcaccgtgga ttttcagcca gtagtaaccc tctttaccga ttggtttacc  10740
tttagccagc gtcagcagac ccttggtcat gtcgttacct tgcgggttga acatagacac  10800
agcgtaaaca cgaccgcgcc agtccatgtt gtaagggaac cagatggcct tatggttagc  10860
gaacttgtta gcttgctcaa tcatgaactc taagctgata cggcgagact tgcgagcctt  10920
gtccttgcga tacacagcag cagcagcacg tttccatgcg gtgagagcct caggattcgt  10980
```

```
gtcgatgtct tccggtttca tcgggagttc ttcacgctca atcgctggga tgtcctctac  11040
agggcagtgc ttccacttgg tgattacgtt ggcgaccgct aggactttct tgttgatttt  11100
ccatgcggtg ttttgcgcaa tgttaatcgc cttgtacacc tcaggcatgt aaacatcttc  11160
gtagcgcatc agtgctttct tgctgtgagt acgcaccagt gccagaggac ggcgaccgtt  11220
agcccaatag ccaccgccag taataccagt ccacggctta ggaggaacta cgcaaggttg  11280
gaacatcggg gagatgccag ccagcgcacc tgcacgggtt gcgatagcct cagcgtattc  11340
cggcgtgagt tcgatagtct cagagtcctg acccactacg ccagcgtttt ggcgatgtaa  11400
gctaaccatt ccggttgact caatgagcat ctcaatgcag cgcaccccta cgtgaatgga  11460
gtcttccttg tgccacgaag accacgcctc gccaccaagt agacccttag agagcatgtc  11520
agcctcgaca acttgcataa atgctttctt gtagacgtga cctacgcgct tgttaagctg  11580
ttcctcaacg cgcttcttga agtgcttagc ttcaaggtca cggatgcgac caaagcgagc  11640
ctcatcctcg atagctcgac cgattgcact ggctacagcc tgaacggttg tattgtctac  11700
gctcgttagg caagccagcg ttgtcttaat ggtgatgtac gctacggctt ccggcttgat  11760
ttcttgcagg aattggaaag ctgttggacg cttgccacgc ttagcttgta cctcctcaaa  11820
ccactcgttg atgcgtgcaa tcatcttggg tagcagggta gcaattagag gctttgcagc  11880
agcgttatca gcaacctcac ccgccttaag ctgacgctca aacatcttgc ggaagcgtgc  11940
ttcacccatc tcgtaagact catgctcaag ggccaactgt tcgcgagcca aacgctcacc  12000
gtaatggtca gccagagtgt tgaacgggat agcagccagt tcgatgtcag agaagtcgtt  12060
cttagcgatg ttaattgtgt tcatttagtg cctcttccag ttagtaaatc gtatctattc  12120
aggccaccct aagtcagatg acctgtaaga taagactatc agcccattag cattgcgtaa  12180
agttgtttgt cgatgttgag cggaagaccg ttagcgatag ccattcggtc agcttgaaac  12240
cagtgcgctg cgactcgttc ctcaagcgcc ttaaagtccc cagagaacat gttgacccag  12300
agcatagcgt tattggttct tcctagtaca tccacagcta cctcatggtt acgccgttct  12360
tgacgttcag cccatcgcca cgcagcaagc attctttcgc gcttagcttt gtgtgcttta  12420
cgtgccttgc ggttgcgacg tttgaatctg cgtaactcca agcgagctac atgacgttct  12480
ttacggtact tagcgcggtc gattgctttc tggcgcgcga cttcctcgac ttccttgatg  12540
agttcctcag ggtcaatgct gaatgcgcca ccgtctttct tctgtgagaa tgataccggg  12600
tcggttatta ctggaacatc actatcatcg aacattatgt tcccactatg catatcgaac  12660
gatgcgattc catcaaagaa cttgcggatt aacttgcaag tctctacaaa ctcaccgtcc  12720
caccccgtga ggtagtcata atccttagag ttacactcaa taacagcact tgcaatatca  12780
gcgtacttgt catgctcctc gttatcacac ggctcacact cattcagggc atcaagcacc  12840
accgtatagc acccagcatg acgctgtacg tcgtagacgt tagggatacc agcgcggccc  12900
tgatacatgc ggcagaatgc ggtatacgca gcacctgagt cctctttctt aaagcccacc  12960
ttaatcactc tgttaggcag cagcgggtga ctataagcag ccgagaagtg accattaccg  13020
agcatcttga aacctgcatc agccgtgaga cacttcaagg tagtccacca atcttggtgc  13080
tcaagtgcct gatttagttc tgtaatttcc ccatcgcatg tctcgctatt gaccatctcg  13140
accagtaagt cgatgagcat accttggcgc ttgtcaagtt cacagattgg tagcgctttg  13200
attgcgtcga tagcgttcat gatgtcggtg atgttcattg tagtgtgtcc tgtatgttcg  13260
ttatgagata gcgttcagtg tgttgattag tgcctgttca agtgctgcac gtttcttggc  13320
tttaactttt tcctttcgcc tgtgccatgc cgccctttct tgctccttgc ggcgttcgag  13380
```

-continued

```
gttgttctct cgccaagttc tgactattcg cctatttgca gcgtatagtg tgccattggg  13440
catatagcct ttctttaagc catcagtgca ttctatcata acgcagtgtc ctttatagtt  13500
taccagttaa ataatggaaa gcgttgcgca atagttcagg tgagtcttta agcaggccta  13560
ttcctctgtt gcagtttgag cacagaagtc cccttacgtc tcccgtaatg tgtgaatggt  13620
caacacacag ttgcctgcct tcaatgcttt caggttgttt gcatatggcg cagaccccat  13680
gttgtgcttc atacatcttg cggtacactg attcatctat accgtagttg atttttagat  13740
ggttgttgcg cctacgcttg gcgtccttga ttgccttatc agttggtgca ccagcagctt  13800
ttgcctttgc tcttcgttcc ttttgctgcc ttgccttgca tttcttacac gtaccgatgt  13860
gaccatctcg tgacgctgcg tttttagtgt acatattgag cggttttatc tcaccacatg  13920
ctatacacat tttggaacaa tgaagcataa agtttccctc agttgcaaga acattcagcc  13980
caattgaaga cgcttgcggt tgatgcgcag ttcacgctta aggcgctcga tacgttgttt  14040
cattgcgaac ccatcaggtg tgcatacggt tgccccgttg gaagtatgga tgggcataac  14100
gtagtgcttc ataccatatt gtttcatcat ttgcgcagtg ctcccgtgat aatacaagcg  14160
accaagtaag cgcccacagc tacacccaaa gactccccaa aggatgcgcc tacagctaga  14220
cctagagcgg tgagtagacc gatagtaaac atatgcatta ctcccattaa agtaaagtga  14280
taatcataaa ggccactcat caggagcgac cttgggttta ccacttggta gacttgaagg  14340
ctgttgtcaa tcgttccaac ctgcacatgt tgcttggtgc atcacacagg cttgatactc  14400
ctcttgcgct aaaatcgggt ttacccaatg tgtgacctgt ttgccgtagc gcacaacgta  14460
ggtgcatccc attgacccgt gatagtactc acgcagcgtt acagtgcatt ggcctttgat  14520
tttagatgtt gccagaagtt tactcatggt gttagtccta ttgcatgttg aatgataatc  14580
atgaaggcca ctcgcatgga gcgaccttga gcctatcact cagcagactc caaggctatt  14640
gccttgttgt tttcgtacag ttccttaagg tgttccattg cgagcgacca gtcgaagcca  14700
catcgcacca tgtcgctata gaatagtaca gtttgagcgg tcagaccgta ttgcgtggtg  14760
ttgttagcca ttactcttcg ccctcttcgt agtcttcctc ttcctcgact tcctcaaggt  14820
actcgttcag taagtcctca gcgtcttccc agaggtcaat cgtgagttgc tcatagatac  14880
gtgcttgcag aatacgaatc acgtccttgg tgtccggcat caggccagag tcttcgaact  14940
caaggtcgat accctcgctt gccattacgc taaagatgtc agcgtagtaa atcggtacgg  15000
cgctatcggc tgcctcatgg attgcatcat gcaggtcatt agtgtcacgg atgtcagcat  15060
aacgaatgtt ttctttcagc atttcatagg cgtggtcgaa aacgttgtga taagtcatgt  15120
tagacatagc cattttgtgt taccccgttg tgtatggtta gtagtggata tcataaaggg  15180
caccttgcga taccettgag ttatccgcta gtcatgcacc caagagctat ttaccagatt  15240
gttaaagagc atgtcggtca ggtttcgtta gaccctagcg cgtttcagtg ttgcgcctca  15300
ctgtcgtttc atgtggtaca tcttacagct tttaaaggag gctgtcaacc tgttattctt  15360
ttgtgcgatg agtgaccgaa ttcgactcat ggctagtgcc ttatccttgg cgggtcgcgg  15420
gcaggtttct cggttcctat ccctacaccc ttactgcatg tggtacatcg taccgtgttt  15480
acttcatgtt gtcaaccagt ttgtttcact ttgtgtgccg tggtgcgctt aagtcaccta  15540
gaagacaccg tgcgtccggt tggcgctgct agtgttacct agcgatttgt atcttactac  15600
atgttactgc gtgttgtcaa tgcctgtttt tcgtatgact tatcaggctg tctacttatc  15660
cggttgaccc cggtatctca gggagtggtt tttgaccgtt gtcccgttga cgagatgaat  15720
```

-continued

```
agtaacctca taggacactt taagtcaata ctctttttta aattatttta atttctctct  15780

tttaagtcct ctttaagtag tctctctctt tagtgagtcg tattaaagac gatggctgaa  15840

gattatctct ttataggtaa caacaaggcg tctttaggga taggctttag gatggtcttt  15900

aggatggtct ttagaattat ctttaagatg ggattgact gaatgggtct ttaagggtat  15960

tctttaggtg ttggcttgat gaatgacttt aggaggatac tttaggagga tactttagga  16020

ggatacttta ggaggctgaa cagataggga cacagagaga cactcccact aacccttagg  16080

accctccctc ggtccacctc aaggcccact ttaaggccac ctcaaggtcg gcactccaaa  16140

ggagtgactt tagggacccc tatgggggga accttaggtg ctta                    16184
```

<210> SEQ ID NO 3
<211> LENGTH: 16799
<212> TYPE: DNA
<213> ORGANISM: Artificial Sequence
<220> FEATURE:
<223> OTHER INFORMATION: a part of DNA of novel bacteriophage CJ20 Contig00003

<400> SEQUENCE: 3

```
catattcatt gacaatcatt tcatttgaaa tcagttgcat atccataata ttttcctcat    60

tagtagcggt tgtaaccccg gggaccaaaa gagttggcac ccaggcgttc atctttcttt   120

ttggctcttg ctctaaaccc agaatcacct gtttgagctt tcagttcttt taacaatttg   180

gccttcaggt cagtaatgaa accaatccgg cggtctccct tgtagacata gattccgtca   240

ttactgtcac catatgcctg tgtaactctt tcatttgtaa ttaagtttaa catgttttag   300

tcctcatcag tagttgatgg aaccattatg tatagaaagg aggggcttgt acaccccttt   360

tttattattc aggaaggatt acttccgctt ggtagtccga cggaatgtaa agtttatgat   420

ttttaaggaa aactttattg atttgagcaa tcgtttgttc ggtttcctgc gggcgttgat   480

atgtgttcat taatacggag aacaatcccg ggtatggttt acacaactct tgacctttaa   540

tcgcaaactc gcgacggtct tttcctgcta actgtttctg ggcatcaagc aacaatccca   600

gcgtattaga cagataatcc agatgtacaa tggtaaaggc attaactttt tcgcgagcat   660

aatcatcacc agtaaacatg gcaataacat catctgcgcc gccggcaaca acaacttcaa   720

acaggcgctc attattatta atggagtctt tagtatggtg cagagcacaa taccattctg   780

ttttcagctt gaacttctga ccacttgcca gctcgtagac gaaaccttca atctctttca   840

taccacgaac attctcaatg ctcaccaggt catatgcttc aaccaggaaa ggacggagtg   900

cagcatcttt gaacagctca ggataaggaa tatattcgcc agtttcatta tgacgaacgt   960

tcagtaaaat caggtcacgt tcctggtaag gcaaaacaat gcggttggtt ggtgcaacat  1020

attccatatt gcatgtataa ccagcttcag tgatttcagt cacacgagcc ctgaacgctt  1080

cacggtgcgg ttgtttaaac acctgcagag attcagcagc ttgggagctt ttaattgacc  1140

ctttggattt aaaagcaata ttggtctggt ccatataagt agaaaccaag ctaccatcag  1200

cttttgcagt aaccaggaca acttcatcaa ggttaaggtc catggtcatt gggttctcac  1260

ccagattaaa gaatttttcc ataggacggg cagcaatgcg aactggacca ttgtcatcca  1320

tttcaaacat aatgccacga cactccagtg catcatcaag aagccaatca ctataggaag  1380

catagttata gctgaagatg cggaacttag tttcaaatgg agaaacaaaa tccgtataga  1440

aaaacttacc tttatcggat tcggcgcaaa gcttcattaa gttatcatat aattcaatca  1500

tttcttcacc ttatgttggt aattccacgg gggattaaaa agcttgatga acatcggctc  1560
```

-continued

```
ttccagagac atcgtttcga ctgacattgt gccaagttca ttggtcattg acagattgaa   1620
acattgtcgt gcatagaata ccaccttttt accttcttgt aaagcttcat gtatcatccg   1680
ggatttgttt gaatcactcg tctggtcgat tcggttaatc gcagtccggt aatagttgat   1740
acgcttctta aggttgttcg tcttaccaat atacactagt tcatcatcaa ctgaaatagc   1800
atagataaca tttttcttgt ttgcgagagt aaggataggg attttaccat cgactaactc   1860
taactccgcg tattttataa aactgtattc atcagcgatt tgtttcatgg gcaaaaaggg   1920
ccgaagccct ttccttatag atatttacgg aaaccagcaa gaacattctc atcgacgtca   1980
ttgtcaatct gggctaccag gtaagcagac aactcaactt cttgtggtgc agattgcaca   2040
ttatcagagt taagatattc gcgaatccat ggaatcgggt gcttagtaga ttctaacacg   2100
atttcacacg ggagaccaca ttgcttcata cgagaaaccg tcaggtaatc gatgaaccgg   2160
ttaagaatct cgacgctcag cccggggagt ccaccatctt taaacagatg tacagcccat   2220
tcctttcct ggcgattgac ttccatgaaa atagctgcgg cttctgcttc acattcgtga   2280
gcaattttaa cccattcgtc accgtcaaca ccagtctgca gctgacgaag aatatattgg   2340
gtccccttaa gatggagctg ttcatcacgg gcgatgaact tcattatctt cgcgttacct   2400
tccatgattt ccatgttctt atggaagttg aaagtacatg caaaagatac ataaaaacga   2460
atagcttcca gcgcgttaat aacatgcagg cagagataaa gagacttcat caatactcgt   2520
ttggcgatag cttcttgttt gatagctcgt tccaaacgtt cgtccgcttc gggagtttct   2580
ttggccagtt caacaaaagc aatctggttt tgccattgac gagtttttatt cagaacatca   2640
tcatagtaat gaccaatgga ttctgcacgc ttcatgattg catcatctaa caggatttcg   2700
tcgaatacct tcgccgggtc cgtatagaga tttcgcatta tgtgcgtata agaacgagag   2760
tgaattgtct cgctgaatgt ccaggtctga atccatgtat caagactcgg gtcagaaact   2820
aatgcggcta atgctgcagc tggagcacga ccctgaatac tatccagaag tgattggtat   2880
ttcaggttgt tggtaaaaat attttgttga tgttcaggaa gcttattaaa ttgggctcca   2940
tccatcatca ggtttacttc ctcaggtcgc cagaagaatg ataattgctt ttctgttaat   3000
tcttcgaaaa ctttatggcg ctggatatca taacgggcaa tccccaatcc tgaaccaaaa   3060
aacatcggct cagctaaaac atccactgga gtggtattaa aaactgtact cattttattt   3120
cctcaatagc tcatccatga gcataattat atcaaagttt acaggcggag cagtcttctg   3180
ctttaggagc ttcgatttcg taatcgtctg ttccggaacc atctcgagtg ttatgataat   3240
aaaggttttt tccaccaaaa taccagaagt acatcaggtc gtcaagcata actgacatcg   3300
gaacttttcc tttcggataa ttctgcgggt cataatatgt attggctgat gctgactgac   3360
aaatccattt caacataatc gcgacttgtg tcagataagg tttgttacct tgcttagcta   3420
gcacccatgc gtaatcgtac aatcctttat tgtgctcaat attgggcacg acttgattaa   3480
aggaaccctc ttttgactct ttaatagaga ctggtccacg cggaggttcg ataccgtttg   3540
tactgttaga aacttgggaa gatgactcac aaggcataag tgctgataat gtgctattac   3600
ggatgccatg cgcaaccagg tcttcccgca actgcgccca gtcacaaacg tagtttggag   3660
ctgcgatttg gtcaatcttt ttattgtacc agtcgatagg taattcgcct cgagcccaac   3720
gagtgtctga ataatattcg caaggtcctt tttctttggc gagtttgatt gatgcacgga   3780
taaggccata ttgtaatctc tcgaacagtt catgcgttaa atcgtttgca tcagtgtagg   3840
aagcgaaatt gcttgccaac catgcagcat agttagtaac cccaacaccc aggttgcggc   3900
gtttttggc tttcagagct tctttaaccg gataaccctg gtagtccaac agattatcaa   3960
```

```
gagcacgaac ttgaacttcg gctagctcgt taatcttatc ttggtcctgc cagtcaaaac   4020
tatccagaac aaatgcagag agggtgcaca atccgatttc agcgtcttcg ctgttcacat   4080
cagtagtcgg gattgcaatt tcgcagcaaa ggtttgattg acgaatcgga gccttatcgc   4140
ggatgaacgg agtgtagtca ttcacgttat cgacgaactg cggataaacc ctggctgtac   4200
cggaacgttc ggtcatgaat aattcaaata catcttttgc tttgatacgt ttcttacgaa   4260
ctgtcgggtc tttttctaag gcttcatata actcacggaa tttatccggg ttatcaaaat   4320
atgaataata caattcaccg ccagcttcgt gtggactaaa cagagtgatg taatcattct   4380
tggccagtcg ttccatcatc aggttattca actggacacc atagtccata tgcctgatac   4440
ggttttcttc aacgcctttg ttgttcttca gaacgagtaa attttcaact tccaaatgcc   4500
aaataggata ataagcagta gcagcgccgc cacggattcc accttgtgaa caggatttaa   4560
cagccgtttg gaaatgtttc cagaacggaa taacaccagt atgcttgact tcacccatac   4620
cgattttcga accttcggca cgaatcatac caacgttgat gccgataccc gcacgcttac   4680
tgatatattc gatgattgaa ttggcagtct tattgattga cttcagggag tcagcagctt   4740
cgataaccac gcaggaactg aactgcctgg taggtgttct ggcgcccgcc atgataggtg   4800
taggcaacga aacctgtcga gtggatactg catcataaaa acggcaaacg tgcttcagac   4860
ggtccgttgg ttcatcctgg tgcagtgcca ttccgatagc catgatagcg aattgtggag   4920
tctcgtagat ttcccagtgg gttttatctt taaccaggta tttctctttc aactgcatcg   4980
cgcctgcata agtcaggtca aaatcgcgtt cgtgcttgat acgagattcc agataagtaa   5040
tctcttcagc cgagtagctt gacaacagct ccgggtcata tttgccttca ttaacacaat   5100
aagaaatctg gtcaataaaa gaacgtggct caaactggcc ataaacatct ttacgcagag   5160
caaacatcgt agccttcgct gcaacgtatt ggtaatctgg ttcttcaacc gagataagcc   5220
cagcagacac tttgatgata accgtctgaa tatcacgagt agtcatacca tcgcgcagat   5280
gtggtttgat tgtttcgtat aattcatacg ggtcgatatt ggttccttca catgaccagg   5340
aaagaacttt aataattttc tggccatcaa aatcttgaga tacgccacta ctttttttgta   5400
cttgcatgtt ttcctctgtt ataaaatggg gtcatgctta tactaacaca tgacccctgg   5460
agcggaatcg tatttataga aggaagttaa gtctgaccat tacgaccaaa aataaaatgc   5520
cagcaatttg aatttgcatt agaccgccat cggtgccgca atcgttggat gtgggtcgta   5580
accttgcaga acaaaatcat ccggggtcat gtgttgagtt acccagtaaa gctgcatctc   5640
ggtatcgaac tgactaaaac cattcgggaa attaatcgat agtttcggca gctgcttcgg   5700
ttcacgttct aagacttctt tacattggtc aatgtggttc atgtagatat gcgtgttacc   5760
acccatgaat accaactcac ccggaaccag ttcacacatt tcggcgacga tatgtaatag   5820
agtaccataa gaaccaatat caaatggcaa acccaggaat acgtcaacgg aacgctgata   5880
ccacaacaag tccagaatac cattatgcac gttgaactga taaagcaagt gacaaggagg   5940
cagagccatt ttatccagtt cagccgggtt ccatgcggat acaatctgac gacggtcatg   6000
tggaacagtt ttaattttgt taataacatc tttcagctgg tcaacaccac cgaaatcacg   6060
ccattgttta ccatacacag gacccagttc gccatcaaca taacctaatg cacgaccttg   6120
tgcttcaaag ttctggtccc agatggtctt tttatcagag tcagggccat gcgtaatttc   6180
acgaagacgt tcaacgttcg tagaaccttc caggaaccac aaaagctcac caacaactgc   6240
acgatatgcc agacgtttaa cagtcgttgc cgggaagcca tcagccatgt cccaacgaac   6300
```

```
tttggtgcca aatgtcgcga tagtaccagt cccagtgcgg tcgtcagtct gatagccaat   6360
gtcaaataca gtttgaatca agtcttgata atttttcatt tatatacagt ctctgtaata   6420
tgggttactt catctatttt ataccaatgg gcttcaagca tttcacgttt gcttatatcg   6480
tacaggaagt cactatccaa ctgtactgtt gagtttacgc gatgcttttt ataaattttg   6540
gtcatgacaa tttcatccgc ataaggtgca gcggcttcta acaatgattt accaccaata   6600
acacagatat aattttctga agaaataaac atttgagcag gagaatctgg cgcggagata   6660
gaaacttttt caccagaaat caatttcaaa taattagccc acgtgatata accacccgcc   6720
aactcaccag cctttgtaac tggatacggt cgcgctgggt cagccacaac gacgtgaaag   6780
cgccctttta atatagacgg taggctttca aaggtttttg ctcccatgag cacgatagag   6840
tttttgtgc gagccttgaa gttctgcagg tcctttttga tatgacccca tggcagacca    6900
tcatcaagtc caaatgcatt ttcatcacga ccatcaactg ttttagttgg agcataagcg   6960
aatactaatt taatcataat ttttcccacc atgcaatagc ttcatttgtg tcatagaaaa   7020
tgtctgcatc tattttaaca ccatctttaa aaagtgtcac tgctgcttta aataattcat   7080
agttgttcac agacatatca gctgcatcat taaaggcctt ttcaaattca ccagcatcag   7140
ggtcatttaa tgcagtgaag agtgtccagc tatcactatc atgatattca aatactacaa   7200
tcattttaat tccttaactg tctttttaat ggcagtaaaa tctttgcgaa tatcgagaat   7260
caatttgtaa agatgtttaa ttgtatctgt atcaaaatat gataccgcgc aacgtgattg   7320
gcgaatatct tctaatgaat atttgctttc acttgtacca tatccaatga taccactaat   7380
gcacttgtca ttaagcgtat atttctgtgg accatcaata ttatttttag gatagatgta   7440
aaggctccaa tcaaattttt gttcaagagt attaacctta acttcaagaa tcagttcagg   7500
atgtgcatca tctttagcaa aacaagtgta ttcagcaagc attatatttt cctcacgctt   7560
tcttagcaac tttccagtca gctttaaatt ggtcaacatc agagtggtga atccagaaac   7620
cagacgagct gccatcttca taaagaggac aaccatcaca ctcatctttc caacccattt   7680
cacacaaagc ttgttcagct ttttccagag cttctggatt gttaccctgg attgtgaagt   7740
accatttacc tttaacttct gaatctttga tgctctcacg ttgtaatttc attttattct   7800
ccagttattt ggtaactcag tatgggacca ttatgtcata gccccatttg gttgtacact   7860
actttttaaa ttttatcaag ccatttgcca agtttaatca tttccttggt ggcttttttcc  7920
atacttctga acttaactaa taaaggatga gtatcaaccc ccataacaag attggttgca   7980
agactgtgtt caccaacaag ccacaatgag tatgtttgaa catcgaggcc ataatttctg   8040
tctttatgaa ctcgtacacc cattacttca aattgttcgc ttgctttttc tactgcatcc   8100
aggaaatcat ctttagtcat attagacccc aaaagttgct ttaatcagtg caatgacttc   8160
tgcggcattt ttatgattta cctgcacatg aatggtttgg gtatcaacat aaggagcatc   8220
gccatcaact tccaggaagt gacagaattc ccattcagcg agttcaaagt actcatcaga   8280
atcccccata ctattcagga tggtgccatc tttcatttca actttttcaa caaaataatc   8340
gccatcaata aagcacatat ccaggacttt gaaggaactg ccatgctgtt ccatcagctt   8400
gactatgcac gaattatcat caggactacc agcgatgaat tgttttttag cagcagggtc   8460
taatacgtaa aatttaccag tttccatcat tttaatttcc tcatttcagt tgggaacata   8520
ttagcatgtt cccgttggtt tgtatactaa gcttcaatca aattcatata aaatttagcg   8580
tcttccgggt gcatcccttc gcaatattca ttttgcataa agcgggtaag gtcttcaaga   8640
ggaccctgga cttcaatttg aacactaaag aattgggtat ctttaatgta agtcatacac   8700
```

```
aaagaaggat aacgattgcg gataacttcg taagtgtatt caaaatcaac gatatcaata   8760
ttaactttag ccattttatt ttcctcatgt agttgatagg cctatagtat ctcaaccata   8820
gacccgttgt aaactgttat ttgaaagctt tttgtagaag ttcaatgatt tggtcgacgt   8880
tattagcatc cacaacacaa ttaatagaaa ccgcccctga aggtgttttt gcataactgg   8940
agtattcgcg gaagcaataa aactcttctt cactaagttc aaaataatca tcacccatgc   9000
catcatcatt atagattgca ccattagcac aaatgatttc ggttacataa tcatagccgt   9060
ctgcacttga tattgattta acttcaaacc aaccgccatt ttcttggatg atgtcgacca   9120
tactagcatt cgatgaacta atatcaatga aagatttaat acgatgtgga ttgaactcat   9180
atttttgcc gatttccatt tttatttcct cagttgttat cagtagttga tggaatcatt   9240
atgccttagc tcaaaggact tgtacactac tttttgaaaa taaaaaaggg acccgaaggt   9300
ccccttatat taaaggccag ccagaaggtc gtcaagacca tcatcagaag gctctggagt   9360
gcttggagca gtcgcagcgc gttcagactt agcaggtttg ctggaagtga agtcttccat   9420
atctttatca aaatcgtcca ggtcagcgcc cagtttatcg gcttgcgcag cagctttaga   9480
agcagcacca ccgagagcag ctgtacccat tactttagag aatttcttct gattctcttc   9540
aagagattta aataccagca attcattcag gtcagacatg tcgtcccaaa gtttttctg   9600
gaatgcttca tcattgatgc cggcgatttc agactggttc atgaatttgg aatcatcgta   9660
gtttttataa ccggaaacca gtttagattt cagtacgaag ttcgcacctt caaaaggaca   9720
agttacatca atagctgttt cgcccatgtc aacatcgact tcaaccatct ggttgatttt   9780
gtccatgatt ttcttaccaa agcgatattt gaatacttga ccttcgttag acggaacagc   9840
agggtcttta atgaccagga tgttagccca gtaagaagta ttacgcttca gtttacgata   9900
ttcggattcg tttgtattgt acaggtcatt cttattcatg tacgcacaca caggacagtt   9960
ttcataatcg ccgtgagtag aagtacagtt ttcaatatac cattgaccag catttttaaa  10020
gccgtggtta acgagcttga tgaatggaga tggattttct tcattcttag aaggcaggaa  10080
acgaataacc gcagagccga cgccatcagt atctttcagt ttccattctt ttttatcgtc  10140
agaagagaaa ccagaaccac ctttaagagc gttaagggaa gcagccaggt cagcagggtt  10200
tttacgttta aacatagaca tatgattttc cttagattat ttgattttta gcagttgttt  10260
tgattacgta ttaattatac ttcaaagtgt ttgaagcgtt atttgacagt ttttaacggt  10320
ctcgatgaac aatttacgag cttcaagaga atctatattt aagattttct tataggcatt  10380
tagtttggtt gaatactttt cccaaaccaa gtcgttagtc tgttcatcat gtttatttat  10440
aatacctaaa aatgaatcaa gcaaacaaaa cgtttcaaat gagataacat tcgattggag  10500
aagtttgaaa atataacttg tattcacttt agtattatac tcgaaaatct cttggagcga  10560
tttgacttcg actttcttac tgaagtaata gatgttcttt atatcatctt cgtatacttg  10620
tctaattctt ttaagtctgc caatgtattc tctgtaaaat atcagagcat cggcatcact  10680
tatatcgcct atccatgcat cctggttcgc aaccaggttt gacatgaata ttaacgttaa  10740
ttctttaaga gtgtacttat cgctaagctt ttcgaaaaaa tacttatcgc gacgtttttg  10800
ataagcacta tcggagattc gcatggtcca gttatatttg ataatatcat aacgacccga  10860
aaaatgctgt ttgatggata agtacagttg gtatactgat ttaccattta tatatcggtt  10920
gttatttgga ggcatgcgaa tcgtaatcat aacaaaaagt ccagcgtatt agttttctgt  10980
gtacgagaca tactcggacg aagcaggtta tcatcatatg cttcattcat aatcttatcg  11040
```

```
acgattcccg cagggatata tcgcgcaaaa ttgccctcag gaattccacg ttcttccaac  11100
caggcagttg tagcttccag ataagacatt tcagttgact cgaccatggc ttcaatatca  11160
agcccgtttt gctgcttact aatcgcccca gaaggcgatt cagttttctg tgtatcaaaa  11220
ttaactaaag aggacatcat agagctccac agcttcggtt ttttcatctt caaaacgctc  11280
acgagtgcct ttatgataca ggccgagctg tgtattgaac atcttaccgt caacgcctaa  11340
ttcagttttt gccttatctt taaggtcttt aatttcgtct gcatatgctt ccatttttaa  11400
tttggtatcg gaagcagctt taatcagctt ggccagttca gcaccatgag tatcaggaca  11460
aaattcaact ttcacttttt tctctttcat aatatacctt aataaaattc agcaatgttt  11520
gcagttagtt tagacagacc agacttaaca aagtaaggat aaactttact tttggctggg  11580
ataacgtagt tattatatcg ttctaagatt gaagcggata tttccgttgg gataaagtcc  11640
atatcaatca acaattggtt ttcacagaat ctattatatt gctcttctgt taaaagcgtt  11700
ttcagcacgt catggtcgta atagttgagc gcaatttgtt caagctcggc tgcacgtgtc  11760
ggtggagtgc gttcaccttc ttcgtgagtg taataaaaat caccacgaac cttgatgctc  11820
gacacgttat ctttttgtc acctttaaca acctttgtca cgcaatccat aagggcatcg  11880
cctgatttag ttttgacata ttttttctgc atcggggacc attgtttcac cccagggaat  11940
ttatgcaact gggtaaagtc accatctgaa gaaacaacca taaccggatg accgagacca  12000
gtgagcaatt ttgttaatac tgcaatatgg tcatcagcct cgactttatc tatattcatc  12060
acgatgtaag gcatatgttt ttccatttca tcgatgatga tgtgcatggc agcatgtaga  12120
ccttcccaat cgaattgaga ctcttcgcga gctttcgcac ggtttttctt ataataataa  12180
gatttcgttc gacgccaata accattcttc gagttatcaa cacaaataat tggaatcgta  12240
taaccgagct tcttgaactg cacgatattt tttcggatag agttcagcac caagtggcgg  12300
gtcattgcag ttgttacctt cggaaagcct gcgtctttgc cgaattcctg gaaggctgca  12360
gccatgatga gctgactaaa atcgagtaac tgaaaaccat ctttttgacg gtcttcttca  12420
gggagtaaaa aatctaaatt catatgaacc tctgttcaat tagttgactc gattatatta  12480
gcataaaatt tttaaagcaa tataaataca cgtataccaa tcaataagga taaagcacat  12540
ggccgatatt ttaaaaccag cattcagagc aacatccggt ctcgatgctg ctggtgagaa  12600
agtcattaat gtcgctaaag ctgattactc agttttgtca gacggcgtta acgtagattt  12660
ctttatagaa gaaaacacag ttcaacaata tgatgcaacg cgtggataca aaaagaactt  12720
cgcagttatc tatgataacc gtatttgggt ttcccaacgc gaaatcgcag aaccagctgg  12780
ctcatttgtt cagcaatatt ggactgcaac ccgtactgac ccgaaatggg aaactgttgc  12840
atctccgact cgtcagctta attccgggga atttatcgcg gtcgactcag ctgcaagctt  12900
taccacattt acattacccc cgaacccgac tgatggtgat accatcgtta ttaaagatat  12960
cggtggtaat accggttata atgaaatcaa agttcaatcg agcaacgtac ctggtcaagg  13020
taaccaaaag attgttcgtt ttggtaatca gtattcagaa gttttaatta caaaaccgtt  13080
ctcttataac atgcttatct tttcaaaccg cttatggcag ttttgggaag ccggtaacga  13140
agaacgcgga ataagaattg aaccaagctc tggtaaatat cgaactcaag catcagattt  13200
tattatgcgt cattatacga ctgcagaaaa aattacattt gttcttccta agtatgctaa  13260
ccaaggtgat attgtcaaat cggtagacat agatggatta gggccattat atcacctgga  13320
tgttgaaacg tttgacgagt caagctctct gggtaaacag ggtcagcaca gtatggaatt  13380
ccgtacaact ggtgatggct tcttcgttta taatgccact gaaaaactgt gggtgacttg  13440
```

ggatggtgat aacaaaactc gcctgcgcgt aatccgtgac agtgtgaaat tgctgtcaaa 13500
cgaaagtatt atcgtgttcg gtaatgataa caacacctcg cagacaatta acatcgacct 13560
tccgacgggt gttcgtccag gggacgtagt taagattgct ctgaactatc ttcgcaaggc 13620
acagactgtt aatattaaag cttcggctac tgataaaatc gcgtcttctg ttcagctgct 13680
ccagttcccg aaacgttcgg aatatccacc ggatactgaa tgggtattgg ttgactcttt 13740
gactttcaat ggtaacataa gttatacgcc agttatcgaa ttaagttatc ttgaagatac 13800
ggttaagaac attaactatt gggttgttgc gcaaaacgtt ccgactgtag aacgagttga 13860
ctcgaaggat gatttgaccc gtgctcgtct gggtgttatt gcattggcta accaggcaca 13920
ggccaacgtt gaccatgaaa ataaccctga aaaagaatta gcaattactc cgcagacttt 13980
ggctaaccgt gtggctactg aatcacgtcg tggtattgca cgaattgcta acactgctca 14040
ggtgaaccag gatacgactt ttgctttcca ggatgatatt atcgtttctc cgaaaaagtt 14100
aaacgaacgt acagctacag aaacaagacg tgggctcgca gaaatcgcca cacagcaaga 14160
aactgatgca ggtatagatg atactacaat catcactcca cgcaagctac aagctcgtca 14220
gggctccgaa agcttatctg gtatcgttaa gtatgttcct actactggga ctactccagc 14280
agcaagccgt ataactgttg ggacaaacgt ttataataaa aatacaacca ctctggtaat 14340
ttctccgaaa gctttggacc aatataaagc tgaccagaat aaccaaggtg ctgtatatct 14400
ggctactcag tcagaagtta acgccggggc aacaaataca ggattcagta actcggtcgt 14460
gactccggaa acattaggtg cacgcagagc aacagattca aaccatggtt taatcgagat 14520
tgcaactcag gctgaaacta atgccggaac cgattatacc agagctgtga ctcctaaaac 14580
gttgaatgac cgtaaagcaa cagaatcatt atccggcata gccgagattg ctacgcaatc 14640
agaatttgat actggcactg atgatactcg tatcgcaacg ccattaaaaa ttaaaactag 14700
acttaataat actgctcgta cttctgttat tgcagcaagt ggtttagtag aaacagggac 14760
gctctgggac cattatacgc tgaatattct tgaagcaaat gagactcaac gtggcactgc 14820
aagactggct actcaacttg aagttaatac tggtactgac gataaaacaa tcgttactcc 14880
gcttaagttg atgtcgaaaa aagccacaga aggcaccgaa ggtattgttc gcatcgctac 14940
tcgcgcagaa actatcgcag gaacaagttc agttctggct gtttctccgg ttagtctgaa 15000
atggattgcg cagtccgaac caacatgggc agcaaccacg acgacccgcg gctttgctaa 15060
gatgtctgaa ggtgcaatta cttttgtcgg taatgcaact gcaggttcga cccaggctct 15120
tgacctgtac gagaaaaata gctatgctat ctctccgtat gagttaaaca aaacccttgg 15180
taacttcctg ccgcgtttag ctaaagccgc agactcggat aaactggata acctggatag 15240
cacgcagttc attcgtcgtg atattgacca aatcgttgaa ggtacattaa cccttagaaa 15300
gaacataaga gttgatggtc agctggcgac tggtggtacc ggtgaatttg gtggctcgtt 15360
ggctgctaac tccacattta ctatacgtaa cacaggaact ccgacccgta tcgttttcga 15420
aaaaggtcct gcatccggtg caaacccggt tcagtcaatg agcatccgtg tgtggggtaa 15480
ccagtatggt ggcggttcgg atacgactcg ttctaccgtg tttgaagttg gtgatgaaac 15540
atctaatcac ttttattcgc aacggaataa tcttggtaat attactttta gtatcaacgg 15600
cacagttcaa ccgattaacg ttaatgcatc cggaacattg aatgctaatg gtgcggcaac 15660
atttggacgt tcggtgactg cacaaggtga atttataacc tatagtgcaa acgcatttag 15720
agctattaat ggacagtacg ggttctttat tcgtaatgat aactcgaaca tctatttcat 15780

-continued

```
gcttacaaat gcaaatgacc agactggtgg ctttaacgga ttaagaccat tagctattag  15840

taatacatct ggccaagtaa cgattggtga aagcttaatc attgccaaag gtgctactat  15900

aaatttgggt ggtttaactg ttaactcgag aattcgttct cagggtacta aacctgcgga  15960

cctttattct agaaaaccta atgcagataa taccggtttc tggtccgttg acgttaatga  16020

cgaagccact tataagcaat tccctggtta tttcaaaatg gttgaaaaga ctaacgaagt  16080

aactggtctg ccttatttgg agcgtggtga agaagttaaa tcacctggta cattgactca  16140

gtttggcaac acgctgaatt cactctatca agactggatt acttatccga atactgctaa  16200

tgcaagcacc actcgttgga ctcgtacatg gcagcagaac aaaaacgcat ggtctggttt  16260

tgttcaggtc tttgatggcg gtaacccacc tcagccgtcg gatattggtg cattgcctgc  16320

tgataacgct tcgatgagta acctgactat cagggattgg ttaagaatcg gtaacgtacg  16380

tattgttccg gacccagtaa ctaaatccgt taaattcgaa tggattgata caccataaga  16440

ggtattatgg aaagatttat ggctgaattt ggacagggat atgtccaagt tcccgtgctt  16500

tctgaaaata acgcagtaag atataaattg tcgattgctg ggacttgtac caaatcgcca  16560

aactatccct acgttaagtt tcaagatgag gccttcgggc ctcagaactt ccaaaatgga  16620

ttaaacctta ttgagattga cccagtaaca aatacaatca ctgcaaccaa aaactatggt  16680

ttcacaaaag actatgatgt catttcacag gcctttgtga cttatattaa ttccattcca  16740

gcgggtagga ttgtttgttt gatatcgcag gggaaattga atgcttccca aactttaat   16799
```

BACTERIOPHAGE AND ANTIBACTERIAL COMPOSITION COMPRISING THE SAME

CROSS REFERENCE TO RELATED APPLICATIONS

This application is the U.S. National Phase Application under 35 U.S.C. §371 of International Application No. PCT/KR2014/001476, filed Feb. 24, 2014, designating the U.S. and published as WO 2014/133289 A1 on Sep. 4, 2014 which claims the benefit of Korean Patent Application No. KR-10-2013-0021498, filed Feb. 27, 2013. Any and all applications for which a foreign and/or a domestic priority is claimed is/are identified in the Application Data Sheet filed herewith and is/are hereby incorporated by reference in their entirety under 37 C.F.R. §1.57.

REFERENCE TO SEQUENCE LISTING

This application incorporates by reference the sequence listing submitted as ASCII text filed via EFS-Web on Aug. 25, 2015, and updated by a file entitled "AIP22.014APC_REPLACEMENT_SEQLIST.txt" which is 90,161 bytes in size, created on Nov. 19, 2015, and last modified on Nov. 25, 2015.

TECHNICAL FIELD

The present invention relates to a novel bacteriophage having a specific bactericidal activity against Enterotoxigenic *Escherichia coli* (ETEC), and an antibacterial composition comprising the same. In addition, the present invention relates to a method of preventing or treating animal diseases using the novel bacteriophage or the antibacterial composition.

BACKGROUND ART

*Escherichia coli* (hereinafter referred to as '*E. coli*') is a Gram-negative, short rod-shaped bacterium belonging to the genus *Escherichia* and the family Enterobacteriaceae, and is one of the normal flora existing in the intestines of various animals including mammals. It was known that most of the strains of *E. coli* are non-pathogenic and may cause opportunistic infections, but some highly pathogenic strains cause diverse intestinal diseases and sepsis in animals including humans.

An example of *E. coli* may include enterotoxigenic *E. coli* (ETEC), enteropathogenic *E. coli* (EPEC), enterohemorrhagic *E. coli* (EHEC), enteroaggregative *E. coli* (EAEC), enteroinvacive *E. coli* (EIEC), necrotoxigenic *E. coli* (NTEC), or the like. It is known that among them, particularly, ETEC generates infectious disease associated with *E. coli* in swine.

Currently, as a large number of swine are collectively bred in a pork industry, colibacillosis in swine has been in the spotlight as a most frequent and troublesome disease (Non-Patent Document 1). Recently, occurrence of swine colibacillosis has increased in Korea, which has caused growth retardation and death of young swine due to diarrhea, resulting in tremendous economic losses to farmers (Non-Patent Document 2).

In order to prevent and treat colibacillosis in swine, many antibiotics have been administered to swine in the prior art, but when antibiotics has been misused or overused, the misused or overused antibiotics may give rise to drug resistance and remain in bodies of the swine. Therefore, currently, the use of antibiotics has been restricted around the world (Non-Patent Document 3).

Meanwhile, bacteriophage is a specialized type of virus that infects and destroys only bacteria, and can self-replicate only inside host bacteria. The bacteriophage has strong host specificity as compared to antibiotics, and recently, a problem of emergence of strain resistant against antibiotics has been serious, such that an interest in practical use of the bacteriophage has increased (Non-Patent Documents 4 and 5).

Therefore, research into the bacteriophage has been actively conducted in various countries around the world, and in addition to a patent application for bacteriophage, an attempt to acquire Food and Drug Administration (FDA) approval for a composition containing the bacteriophage has been gradually increased.

As the prior art for the bacteriophage, 7 kinds of bacteriophages for controlling *E. coli* 0157:H have been disclosed in Patent Document 1, and a bacteriophage having a specific bactericidal activity against *Staphylococcus aureus* has been disclosed in Patent Document 2. Further, lytic protein derived from a bacteriophage specifically destroying a peptidoglycan structure of bacterial cell membrane, and bacteria lysates by the lytic protein have been disclosed in Patent Document 3.

However, in spite of presence of the following prior arts, a technology associated with the bacteriophage for preventing and/or treating infectious diseases by ETEC that are a still important problem in an livestock industry including the pork industry is still insufficient, such that a bacteriophage and a technology associated with the bacteriophage should be developed.

PRIOR ART DOCUMENT

Patent Document (Patent Document 1) U.S. Pat. No. 6,485,902

(Patent Document 2) Korea Patent Registration No. 10-0910961 B1

(Patent Document 3) Korean Patent Laid-Open Publication No. 10-2009-0021475 A

Non-Patent Document (Non-Patent Document 1) Young II Park, Swine production science, Sunjin Publishing group, 353-359, 1998

(Non-Patent Document 2) Eu Chul Hong, master's thesis, Dankook University, Addition Effect of Egg Yolk in Early Weaned Piglets, 2001

(Non-Patent Document 3) Mason H S et al., Trends in Biotech, 13:388-392, 1995

(Non Patent Document 4) Cislo M, et al., Arch. Immunol. Ther. Exp. 2:175-183, 1987 Arch Immunol. Ther. Exp. 2:175-183, 1987

(Non Patent Document 5) Sung Hun Kim et al., Bacteriophage, novel alternative antibiotics, BioWave Vol. 7 No. 15, 2005, BRIC

DISCLOSURE

Technical Problem

The present inventors conducted studies in order to solve problems such as resistant bacteria occurring upon the use of antibiotics, antibiotics remaining in meat, and the like, and efficiently prevent and treat infectious diseases by pathogenic *E. coli*, and as a result, the present inventors isolated new bacteriophage ΦCJ20 (KCCM11362P) having a specific bactericidal activity against ETEC from the nature.

In addition, the present inventors identified morphological, biochemical, and genetic characteristics of the novel bacteriophage and confirmed that the bacteriophage had excellent acid resistance, heat resistance, and the like, thereby developing an antibiotic, a disinfectant, a feed additive, and other compositions using the novel bacteriophage. Further, the present inventors developed a composition for preventing or treating infectious diseases by *E. coli*, and a method of preventing or treating the disease using the composition.

The present invention provides a novel bacteriophage ΦCJ20 (KCCM11362P) having a specific bactericidal activity against ETEC.

In addition, the present invention provides a composition for preventing and/or treating infectious diseases by ETEC containing the bacteriophage ΦCJ20 (KCCM11362P) as an active ingredient.

Further, the present invention provides an antibiotic, a feed additive, a drinking water additive, a disinfectant, or a cleaner containing the bacteriophage ΦCJ20 (KCCM11362P) as an active ingredient.

Furthermore, the present invention provides a method of preventing and/or treating infectious diseases by ETEC in animals except for humans using the bacteriophage ΦCJ20 (KCCM11362P) or a composition containing the bacteriophage ΦCJ20 (KCCM11362P) as an active ingredient.

Technical Solution

According to an exemplary embodiment of the present invention, there is provided a novel bacteriophage ΦCJ20 (KCCM11362P) having a specific bactericidal activity against enterotoxigenic *Escherichia coli* (ETEC).

According to another exemplary embodiment of the present invention, there is provided a composition for preventing or treating an infectious disease caused by ETEC, the composition containing the bacteriophage ΦCJ20 (KCCM11362P) as described above as an active ingredient.

According to another exemplary embodiment of the present invention, there are provided an antibiotic, a feed additive, a drinking water additive, a disinfectant, or a cleaner containing the bacteriophage ΦCJ20 (KCCM11362P) as described above as an active ingredient.

According to another exemplary embodiment of the present invention, there is provided a method of preventing or treating an infectious disease caused by ETEC, comprising administering the bacteriophage ΦCJ20 (KCCM11362P), or the composition containing the bacteriophage ΦCJ20 as described above as an active ingredient to animals except for humans.

Advantageous Effects

The bacteriophage ΦCJ20 (KCCM11362P) according to the present invention has an effect of specifically killing enterotoxigenic *Escherichia coli* (ETEC).

In addition, the bacteriophage ΦCJ20 (KCCM11362P) according to the present invention has excellent acid resistance and heat resistance, such that the bacteriophage ΦCJ20 (KCCM11362P) may be used as a material for preventing or treating infectious diseases by ETEC in various temperature or pH ranges and utilized as an antibiotic, a feed additive, a drinking water additive, a disinfectant, a cleaner, or the like.

Further, according to the present invention, infectious diseases by ETEC may be prevented or treated by administering the bacteriophage ΦCJ20 (KCCM11362P) or a composition containing the bacteriophage ΦCJ20 (KCCM11362P) as an active ingredient to animals except for humans.

BEST MODE

Figure 1:
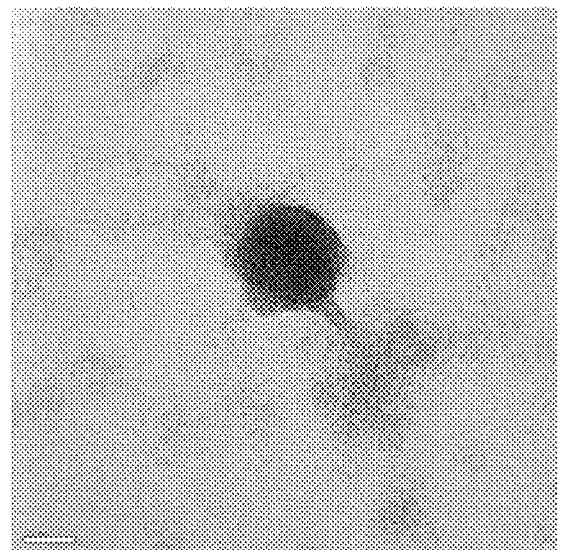
FIG. 1 is an electron microscope photograph of a novel bacteriophage ΦCJ20 (KCCM11362P, hereinafter, referred to as 'ΦCJ20').

Hereinafter, the present invention will be described in detail. Since contents that are not described in the present specification may be sufficiently recognized and inferred by those skilled in the art or similar art, a description thereof will be omitted.

In detail, one general aspect, the present invention provides a novel bacteriophage ΦCJ20 (KCCM11362P) having a specific bactericidal activity against enterotoxigenic *Escherichia coli* (ETEC).

ETEC, which is a Gram-negative, rod-shaped bacterium, is an aerobic or facultative anaerobic bacterium decomposing lactose or fructose to produce acid and gas. ETEC well grows in a general medium and may grow at about 7 to 48° C., and an optimal growth temperature is about 35 to 37° C. In addition, ETEC may grow in a pH range of 4.5 to 9.

Since ETEC produces enterotoxins similar to that of *Vibrio cholerae*, in the case of infection of ETEC, disease symptoms similar to those of cholera are exhibited. The produced toxins are divided into two kinds, that is, a heat-labile enterotoxin (LT) and a heat-stable enterotoxin (ST). The heat-labile enterotoxin means an enterotoxin losing its activity in the case of heating at 60° C. for 10 minutes, and the heat-stable enterotoxin means an enterotoxin that does not lose its activity but has resistance even in the case of heating at 100° C. for 30 minutes.

In the case in which a concentration of ETEC arrives at $10^7$ cfu (colony formation unit) to $10^8$ cfu per a unit volume (1 ml) of serous fluid while ETEC proliferates in an upper portion of intestine, ETEC causes infectious diseases by *E. coli* such as colibacillosis.

A bacteriophage is a bacteria-specific virus infecting specific bacteria to suppress and inhibit growth of the bacteria and means a virus including single or double stranded deoxyribonucleic acid (DNA) or ribonucleic acid (RNA) as a genetic material.

The bacteriophage ΦCJ20 according to the present invention, which is a bacteriophage species-selectively infecting ETEC, has a structure of isometric capsid but a tail is not observed (FIG. 1), and morphologically belongs to Podoviridae.

The bacteriophage ΦCJ20, which was a bacteriophage newly isolated by the present inventors, was deposited at Korean Culture Center of Microorganisms (361-221, Hongjedong, Seodamun-gu, Seoul, Korea) as a deposition number KCCM11362P on Jan. 30, 2013.

In another general aspect, the present invention provides a composition for preventing or treating infectious diseases by ETEC containing the bacteriophage ΦCJ20 as an active ingredient.

Since the bacteriophage ΦCJ20 has an antibacterial activity capable of specifically killing ETEC, the bacteriophage ΦCJ20 may be used to prevent or treat diseases generated by infection of ETEC. An example of the infectious disease caused by ETEC may include preferably colibacillosis, more preferably colibacillosis in swine, but is not limited thereto.

The term "colibacillosis" as used herein means a disease caused by infection of an animal with pathogenic *E. coli*, and shows symptoms such as sepsis, diarrhea (neonatal diarrhea and post-weaning diarrhea), toxemia (edema and cerebrospinal angiopathy), or the like. Among them, sepsis is an acute systemic infection that frequently occurs in 2 to 3 days after birth and has a high mortality rate. Diarrhea is the most common outcome of gastrointestinal tract infections that occur during the lactation period within 1-2 weeks after birth and immediately after the weaning period, and causes death or growth retardation Toxemia mainly occurs in 8-12 week-old piglets after the weaning period, and is frequently accompanied by edema and neurologic signs, followed by sudden death.

The term "prevention" as used herein refers to all actions of providing the bacteriophage ΦCJ20 and/or the composition containing the bacteriophage ΦCJ20 as the active ingredient to animals except for humans to suppress the corresponding disease or retard disease occurring.

The term "treatment" as used herein refers to all actions of providing the bacteriophage ΦCJ20 and/or the composition containing the bacteriophage ΦCJ20 as the active ingredient to animals except for humans to thereby allow the symptom of the corresponding disease caused by infection to get better or be alleviated.

The composition for preventing or treating the infectious disease caused by ETEC according to the present invention may contain the bacteriophage ΦCJ20 in an amount of preferably $5\times10^2$ to $5\times10^{12}$ pfu/ml, more preferably, $1\times10^6$ to $1\times10^{10}$ pfu/ml.

The composition for preventing or treating the infectious disease caused by ETEC according to the present invention may further contain a pharmaceutically acceptable carrier and be formulated together with the carrier to thereby be provided as food, a drug, a feed additive, a drinking water additive, and the like. The term 'Pharmaceutically acceptable carrier' as used herein means a carrier or a diluent that does not stimulate living organism nor inhibit biological activity and properties of an administered compound.

A kind of carrier usable in the present invention is not particularly limited, and any carrier may be used as long as it is generally used in the art and is pharmaceutically acceptable. As a non-restrictive example of the carrier, there are normal saline, sterile water, buffered saline, Ringer's solution, an albumin injection solution, a dextrose solution, a maltodextrin solution, glycerol, ethanol, and the like. One or a mixture of at least two of these carriers may be used.

In addition, if necessary, another general additive such as an antioxidant, a buffer, a bacteriostatic agent, and/or the like, may be further added and used, and the composition may be formulated into an injection formulation such as an aqueous solution, suspension, emulsion, or the like, pills, capsules, granules, tablets, or the like by additionally adding a diluent, a dispersant, a surfactant, a binder, a lubricant, and/or the like, and then used.

An administration method of the composition for preventing or treating infectious diseases by ETEC is not particularly limited, but any method generally used in the art may be used. As a non-restrictive example of the administration method, the composition may be orally or parenterally administered.

As a non-restrictive example of the formulation for oral administration, there are troches, lozenge, tablets, aqueous suspensions, oily suspensions, prepared powder, granules, emulsions, hard capsules, soft capsules, syrups, elixirs, or the like.

In order to formulate the composition according to the present invention into a formulation such as a tablet, a capsule, or the like, the formulation may further contain a binder such as lactose, saccharose, sorbitol, mannitol, starch, amylopectin, cellulose, gelatin; an excipient such as dicalcium phosphate, or the like; a disintegrant such as corn starch, sweet potato starch, or the like; a lubricant such as magnesium stearate, calcium stearate, sodium stearyl fumarate, polyethylene glycol wax, or the like. In the case of the capsule formulation, the formulation may additionally contain a liquid carrier such as fatty oil in addition to the above-mentioned materials.

As a parenteral administration method, an intravenous administration method, an intraperitoneal administration method, an intramuscular administration method, a subcutaneous administration method, a local administration method, or the like, may be used. In addition, a method of applying or spraying the composition onto a disease site may also be used, but the present invention is not limited thereto.

An example of the formulation for parenteral administration may include injection formulations for subcutaneous injection, intravenous injection, intramuscular injection, or the like; suppository formulations; spray formulations such as aerosol formulations capable of being inhaled through respiratory system, or the like, but the present invention is not limited thereto. In order to formulate the composition into the injection formulation, the composition according to the present invention may be mixed with a stabilizer or a buffer in water to thereby prepare a solution or suspension, and then, the prepared solution or suspension may be formulated in a unit dose for an ampoule or vial. In the case of formulating the composition into the spray formulation such as the aerosol formulation, or the like, a propellant, or the like, may be mixed together with an additive so that a water-dispersed condensate or wet powder is dispersed.

A suitable application, spray, or administration dose of the composition for preventing or treating infectious diseases by ETEC may be variously determined depending on factors such as age, weight, sex, degree of symptom of disease, a kind of food, excretion rate of administration target animals, or the like, as well as a method of formulating the composition, an administration method, an administration time and/or route. Generally, a veterinarian having ordinary skill in the art may easily determine and prescribe an effective dose for the desired treatment.

In another general aspect, the present invention may provide an antibiotic containing the bacteriophage ΦCJ20 as an active ingredient.

The term 'antibiotic' as used herein means an agent capable of being provided to animals including humans in a drug form to thereby kill bacteria, and corresponds to a concept collectively indicating a preservative, a disinfectant, and an antibacterial agent.

The antibiotic containing the bacteriophage ΦCJ20 according to the present invention as the active ingredient may have high specificity to ETEC as compared to an antibiotic according to the prior art to thereby not kill beneficial bacteria but kill specific pathogenic bacteria, and does not induce drug resistance, such that the antibiotic according to the present invention may be provided as a novel antibiotic having an elongated lifespan as compared to the antibiotic according to the prior art.

In another general aspect, the present invention may provide a feed additive or a drinking water additive containing the bacteriophage ΦCJ20 as an active ingredient.

The feed additive and the drinking water additive according to the present invention may be used in a manner in which the bacteriophage ΦCJ20 or the composition containing the bacteriophage ΦCJ20 is individually prepared in a feed additive or drinking water additive form and then mixed with a feed or drinking water, or in a manner in which the bacteriophage ΦCJ20 or the composition containing the bacteriophage ΦCJ20 is directly added at the time of preparing the feed or the drinking water.

The bacteriophage ΦCJ20 or the composition containing the bacteriophage ΦCJ20 used as the feed additive or drinking water additive according to the present invention may be in a liquid state or dried state, and preferably, in a dried powder form.

A drying method for preparing the feed additive and the drinking water additive according to the present invention in the dried powder form is not particularly limited, but a method generally used in the art may be used. As a non-restrictive example of the drying method, there is a natural air drying method, natural drying method, a spray drying method, a freeze-drying method, or the like. One method of these methods may be used alone or at least two methods may be used together with each other.

Another non-pathogenic microbe may be additionally added to the feed additive or drinking water additive. A non-restrictive example of the microbe capable of being added may be selected from a group consisting of *bacillus* sp. capable of producing protease, lipase, and/or sugar converting enzyme such as *bacillus subtilis*, or the like; *Lactobacillus* sp. having physiological activity and degradation activity for an organic material under anaerobic conditions such as cow's stomach; mold fungi having effects of increasing a weight of domestic animal, a milk yield, and digestibility of the feed such as *Aspergillus oryzae*, or the like; and yeasts such as *Saccharomyces cerevisiae*, or the like. One or a mixture of at least two of these microbes may be used.

The feed additive or the drinking water additive containing the bacteriophage ΦCJ20 according to the present invention as the active ingredient may further contain other additives, as needed. As a non-restrictive example of the usable additive, there are a binder, an emulsifier, a preservative, and the like, which are added in order to prevent quality of the feed or driving water from being deteriorated; amino acids, vitamins, enzymes, probiotics, flavoring agents, non-protein nitrogen compounds, silicates, buffers, coloring agents, extractants, oligosaccharides, and the like, which are added in order to increase utility of the feed or drinking water. Otherwise, the additive may further include a feed mixing agent, or the like. One or a mixture of at least two of these additives may be used.

The feed additive may be contained at a content of 0.05 to 10, more preferably 0.1 to 2 parts by weight based on 100 parts by weight of the feed. The drinking water additive may be contained at a content of 0.0001 to 0.01, more preferably 0.001 to 0.005 parts by weight based on 100 parts by weight of the drinking water. The activity of the bacteriophage ΦCJ20 against ETEC may be sufficiently exhibited in the above-mentioned range.

In another general aspect, the present invention provides a feed or drinking water prepared by adding a feed additive or a drinking water additive containing the bacteriophage ΦCJ20 as an active ingredient or directly adding the bacteriophage ΦCJ20.

The feed used in the present invention is not particularly limited, but any feed generally used in the art may be used. A non-restrictive example of the feed may include plant feeds such as grains, roots and fruit, food processing byproducts, algaes, fiber, pharmaceutical byproducts, fats, starches, cucurbitaceous, or grain byproducts; and animal feeds such as proteins, inorganic materials, fats, minerals, single cell proteins, animal planktons, or foods. One or a mixture of at least two of these feeds may be used.

The drinking water used in the present invention is not particularly limited, but any drinking water generally used in the present invention may be used.

In another general aspect, the present invention may provide a disinfectant or a cleaner containing the bacteriophage ΦCJ20 as an active ingredient. A formulation of the disinfectant or cleaner is not particularly limited, but the disinfectant or cleaner may be formulated into any formulation known in the art.

The disinfectant may be sprayed in order to remove ETEC onto a region in which animals live, a slaughterhouse, a mortality generation area, a cooking place or cooking equipment, or the like, but the present invention is not limited thereto.

The cleaner may be used to wash skin's surfaces or each of the sites of bodies of animals exposed or to be exposed to ETEC, but the present invention is not limited thereto.

In another general aspect, the present invention provides a method of preventing or treating infectious diseases by using the bacteriophage ΦCJ20 or the composition comprising the bacteriophage ΦCJ20 as an active ingredient.

In detail, the method of preventing or treating infectious diseases according to the present invention may include administering the bacteriophage ΦCJ20 or the composition containing the bacteriophage ΦCJ20 as the active ingredient to targets infected by ETEC or being at risk of infection of ETEC except for humans in a pharmaceutically effective dose. It will be apparent to those skilled in the art that when the pharmaceutical composition is administered to patient, the suitable total daily dose may be determined by an attending physician or veterinarian within the scope of sound medical judgement.

A specific pharmaceutically effective dose of the bacteriophage ΦCJ20 or the composition containing the bacteriophage ΦCJ20 as the active ingredient for a specific animal may be determined by considering an administration time and an administration route of the bacteriophage ΦCJ20 or the composition containing the bacteriophage ΦCJ20, a secretion rate of the composition, a therapy duration period, or the like, in addition to a kind and a degree of the desired response, an age, a weight, a general healthy state, sex, or diet of the corresponding individual. In addition, the pharmaceutically effective dose may be variously changed according to various factors such as ingredients of drugs or other compositions simultaneously or separately used and similar factors well known in a medical field.

The bacteriophage ΦCJ20 according to the present invention or the composition containing the bacteriophage ΦCJ20 as the active ingredient may be administered as a pharmaceutical form (nasal spray) to animals or administered in a method of directly added to a feed or drinking water of the animals and then feeding the feed or drinking water. In addition, the bacteriophage ΦCJ20 or the composition containing the same may be mixed in a feed or drinking water in a form of a feed additive or drinking water additive and then administered.

The administration route and administration method of the bacteriophage ΦCJ20 according to the present invention or the composition containing the bacteriophage ΦCJ20 as the active ingredient are not particularly limited, but any administration route and administration method may be used as long as the bacteriophage ΦCJ20 or the composition containing the same may arrive at the corresponding target tissue. That is, the bacteriophage ΦCJ20 or the composition containing the bacteriophage ΦCJ20 as the active ingredient may be administered through various oral or parenteral routes. As a non-restrictive example of the administration route, oral, rectal, local, intravenous, intraperitoneal, intramuscular, intraarterial, subcutaneous, and nasal administration, inhalation, or the like, may be performed.

Hereinafter, the present invention will be described in detail through the Examples. However, these Examples are only to illustrate the present invention, and a scope of the present invention is not limited to these Examples.

Example 1

Isolation of Bacteriophage Infecting ETEC

Example 1-1

Screening of Bacteriophage and Isolation of Single Bacteriophage

After 50 ml of a sample obtained from pig feces and environmental samples of Samwhaw Gps. Breeding Agri. in Gwangcheon area, Hong seong-gun, Chungchong Province was centrifuged at 4,000 rpm for 10 minutes, the supernatant was filtered with a 0.45 μm filter to prepare a sample solution, and then a soft agar overlay method was performed using the prepared sample solution. The soft agar overlay method is a method of observing a lysis action of bacteriophage using host cells growing in top agar (attached onto a solid medium using 0.7% agar).

In detail, 18 ml of the sample filtrates was mixed with 150 μl of a shake culture solution ($OD_{600}$=2) of ETEC (SNU105) obtained from College of Veterinary Medicine, Seoul National University and 2 ml of 10× Luria Bertani (LB) medium (tryptone 10 g/l; yeast extract 5 g/l; and NaCl 10 g/l) and cultured at 30° C. for 18 hours. Then, the culture solution was centrifuged at 4,000 rpm for 10 minutes, and the supernatant was filtered with a 0.45 μm filter. Then, after a mixed solution of 3 ml of 0.7% (w/v) agar and 150 μl of the shake culture solution ($OD_{600}$=2) of ETEC (SNU105) was poured and hardened onto a LB plate medium, 10 μl of the sample solution was dropped thereon, followed by culturing at 30° C. for 18 hours. Then, it was confirmed that a plaque was formed.

Since it is known that one kind of bacteriophage is present in a single plaque, separation of a single bacteriophage from the formed plaque was attempted. In detail, the plaque was added to 400 μl of a SM solution (NaCl (5.8 g/l); $MgSO_4 7H_2O$ (2 g/l); 1M Tris-Cl (pH 7.5, 50 ml)) and left at room temperature for 4 hours, thereby obtaining a bacteriophage solution. Thereafter, 100 μl of the bacteriophage solution was mixed with 5 ml of 0.7% (w/v) agar and 150 μl of the shake culture solution ($OD_{600}$=2) of ETEC (SNU105), followed by performing the soft agar overlay method using a LB medium having a diameter of 150 m. The culturing was performed until ETEC was completely lysed. After the culturing was terminated, 5 ml of the SM solution was added to the LB plate medium and left at room temperature for 4 hours, thereby obtaining a bacteriophage solution.

After the solution was recovered and 1% (v/v) chloroform was added thereto, the mixture was mixed for 10 minutes, followed by centrifugation at 4,000 rpm for 10 minutes, thereby obtaining a supernatant. The obtained supernatant was filtered with a 0.45 μm filter, thereby obtaining a final sample.

Examples 1

Large-Scale Culture and Purification of Bacteriophage

The bacteriophage obtained in Example 1-1 was cultured at large scale using ETEC (SNU105), and then the bacteriophage was purified therefrom.

In detail, after ETEC (SNU105) was shake-cultured, and an aliquot of $1.5\times10^{10}$ cfu was centrifuged at 4000 rpm for 10 minutes and then resuspended in 4 ml of the SM solution. The bacteriophage of $1.5\times10^{6}$ pfu was inoculated thereto (multiplicity of infection (MOI)=0.0001), and left at room temperature for 20 minutes. Thereafter, the solution was inoculated into 150 ml of the LB medium and cultured at 30° C. for 5 hours.

After the culturing was terminated, chloroform was added at an amount of 1% (v/v) of a final volume and stirred for 20 minutes. Then, restriction enzymes DNase I and RNase A were added so as to have a final concentration of 1 μg/ml, respectively, and the solution was left at 30° C. for 30 minutes. Then, NaCl and polyethylene glycol (PEG) were added so as to have final concentrations of 1M and 10% (w/v), respectively, and further left at 4° C. for 3 hours, followed by centrifugation at 4° C. and 12,000 rpm for 20 minutes, thereby obtaining precipitates.

The obtained precipitate was suspended in 5 ml of a SM solution and left at room temperature for 20 minutes. Then, 1 ml of chloroform was added thereto and stirred, followed by centrifugation at 4° C. and 4,000 rpm for 20 minutes, thereby obtaining a supernatant. Thereafter, the supernatant was filtered with a 0.45 μm filter, and ultracentrifugation (35,000 rpm, 1 hour, 4° C.) using a glycerol density gradient method (density: 40%, 5% glycerol) was performed, thereby purifying the bacteriophage.

The present inventor designated the bacteriophage obtained by extracting the sample from pig feces and having the specific bacteriocidal activity against ETEC as "Bacteriophage ΦCJ20" and deposited the bacteriophage at Korean Culture Center of Microorganisms (361-221, Hongjedong, Seodamun-gu, Seoul, Korea) as a deposition number KCCM11362P on Jan. 30, 2013.

Example 2

Examination of ΦCJ20 Infection on *E. coli*

In order to confirm whether or not the bacteriophage ΦCJ20 purified in Example 1 has a lytic activity on *E. coli* species other than ETEC (SNU105), cross infection with other *E. coli* species was performed.

In detail, 2 kinds of ETEC (SNUJG280 and SNU105) strains and 11 kinds of non-pathogenic *E. coli* strains (MC4100, BL21(DE3), Rosetta (DE3), 2616, 281, 1917, DH5a, GM2929, Tuner (DE3), W3110, and K12G) were cultured, thereby obtaining culture solutions, respectively. Then, each of the culture solutions and the purified bacteriophage ΦCJ20 were used to perform the soft agar overlay method, and whether or not a plaque was formed was confirmed.

The results were shown in the following Table 1.

TABLE 1

| (Serotype) | strain | Plaque formation |
|---|---|---|
| Non-pathogenic *E. coli* | MC4100 | ○ |
| | BL21(DE3) | ○ |
| | Rosetta(DE3) | ○ |
| | 2616 | x |
| | 281 | x |
| | 1917 | ○ |
| | DH5a | ○ |
| | GM2929 | ○ |
| | Turner | ○ |
| | W3110 | ○ |
| | K12G | ○ |
| ETEC | SNUJG280 | ○ |
| | SNU105 | ○ |

As shown in Table 1, it may be confirmed that the bacteriophage ΦCJ20 purified in Example 1 had the lytic activity on 9 kinds of non-pathogenic *E. coli* strains (MC4100, BL21(DE3), Rosetta (DE3), 1917, DH5a, GM2929, Tuner (DE3), W3110, and K12G) but did not have lytic activity on the residual 2 kinds of non-pathogenic *E. coli* strains (2616 and 281) among the non-pathogenic *E. coli* strains.

Example 3

Observation of Morphology of ΦCJ20

The bacteriophage ΦCJ20 purified in Example 1 was diluted in a 0.01% gelatin solution, and then fixed in a 2.5% glutaraldehyde solution. The fixed bacteriophage was dropped onto a carbon-coated mica plate (ca. 2.5×2.5 mm), adapted thereto for 10 minutes, and washed with sterile distilled water. A carbon film was mounted on a copper grid, stained with 2% uranyl acetate for 30 to 60 seconds, dried, and investigated using a transmission electron microscope (JEM-1011, 80 kV, magnification: ×120,000 to ×200,000) (FIG. 1).

FIG. 1 is an electron microscopy photograph of the bacteriophage ΦCJ20. It may be appreciated that the bacteriophage ΦCJ20 has an isometric capsid but does not have a tail, such that the bacteriophage ΦCJ20 morphologically belongs to Podoviridae.

Example 4

Genomic DNA Size Analysis of ΦCJ20

Genomic DNA was extracted from the bacteriophage ΦCJ20 purified in Example 1.

In detail, 20 mM ethylenediaminetetraacetic acid (EDTA), 50 μg/ml proteinase K, and 0.5% (w/v) sodium dodecyl sulfate (SDS) were added to a culture solution of the purified bacteriophage ΦCJ20 and left at 50° C. for 1 hour. An equal volume of phenol (pH 8.0) was added and stirred, followed by centrifugation at room temperature and 12,000 rpm for 10 minutes, thereby obtaining a supernatant.

The supernatant was mixed with an equal volume of PC (phenol:chloroform=1:1) and centrifuged at room temperature and 12,000 rpm for 10 minutes, thereby obtaining a supernatant. The supernatant was mixed with an equal volume of chloroform and centrifuged at room temperature and 12,000 rpm for 10 minutes, thereby obtaining a supernatant. The obtained supernatant was sequentially mixed with 10% (v/v) of 3M sodium acetate and a double volume of cold 95% ethanol, based on the total volume, and left at −20° C. for 1 hour. Subsequently, centrifugation was performed at 0° C. and 12,000 rpm for 10 minutes, and the precipitate was obtained by removing the supernatant. Then, 50 μl of Tris-EDTA (TE) buffer (pH 8.0) was added thereto to thereby dissolve the obtained precipitate. The extracted DNA was diluted 10 times, and a concentration was measured by measuring absorbance at $OD_{260}$.

Figure 2:
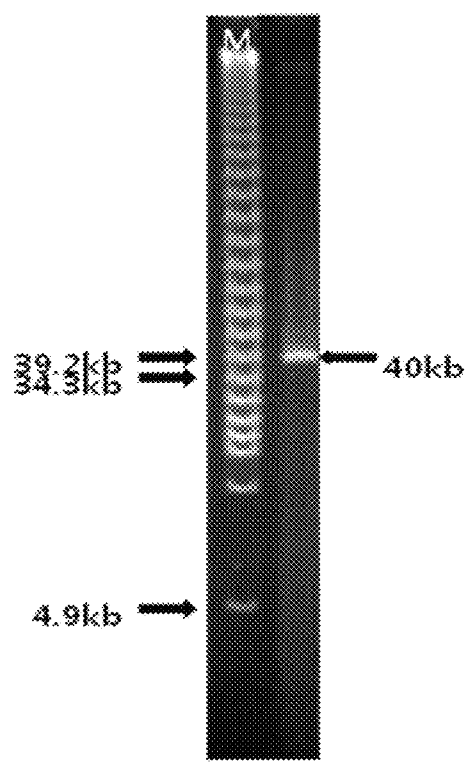
FIG. 2 shows a result of pulsed field gel electrophoresis (PFGE) of the novel bacteriophage ΦCJ20.

Next, 1 μg of DNA was loaded onto 1% pulse-field gel electrophoresis (PFGE) agarose gel, and electrophoresis was performed at room temperature for 20 hours using a BIO-RAD PFGE system program 7 (size range: 25-100 kb; switch time ramp: 0.4-2.0 seconds, linear shape; forward voltage: 180 V; reverse voltage: 120 V) (FIG. 2).

FIG. 2 is a pulsed field gel electrophoresis (PFGE) photograph of the genomic DNA of the bacteriophage ΦCJ20, and it may be confirmed that the genomic DNA of the bacteriophage ΦCJ20 has a size of about 40 kb. In FIG. 2, M is DNA that becomes a standard for measuring a molecular weight.

Example 5

Protein Pattern Analysis of ΦCJ20

15 μl of purified bacteriophage ΦCJ20 solution at a titer of $10^{10}$ pfu/ml was mixed with 3 μl of a 5×SDS sample solution, and heated for 5 minutes. Then, 12% SDS-PAGE was performed (FIG. 3).

Figure 3:
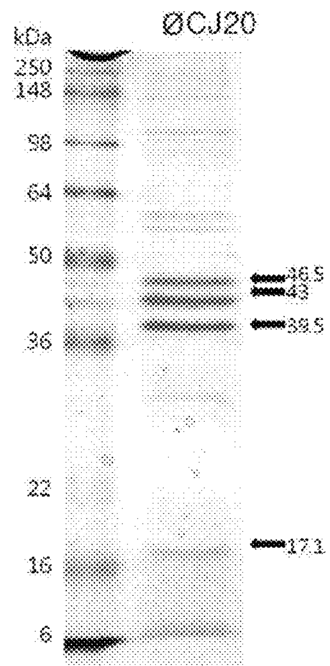
FIG. 3 shows a sodiumdodecylsulfate-polyacrylamide gel electrophoresis (SDS-PAGE) result of the novel bacteriophage ΦCJ20.

FIG. 3 is an electrophoresis photograph showing a result of SDS-PAGE performed on the bacteriophage ΦCJ20, and main proteins having sizes of about 46.5 kDa, 43 kDa, 39.5 kDa, and 17.1 kDa were observed.

Example 6

Genetic Characteristics Analysis of ΦCJ20

In order to confirm genetic characteristics of the bacteriophage ΦCJ20 purified in Example 1, DNA of the bacteriophage ΦCJ20 was analyzed using a FLX titanium sequencer (Roche), which is a gene analysis apparatus. Genes was assembled at Macrogen INC. using GS and de novo assembler software (Roche). Sequence analysis of an open reading frame was performed using GeneMArk.hmm, Glimmer v3.02, and FGENESB software. Identification of the open reading frame was performed using BLASTP and InterProScan program.

The genome sequence of the bacteriophage had various similarities with that of the existing reported bacteriophage, but it was confirmed that a bacteriophage of which all of the fractions were completely (100%) equal to those of the bacteriophage of the present invention did not exist. Therefore, it may be confirmed that the bacteriophage was a newly isolated bacteriophage.

The following Table 2 shows results obtained by comparing homologues of the genome sequence of the ΦCJ20 and decoded genome sequences of other bacteriophages, and partial genome sequence of the ΦCJ20 was shown below.

TABLE 2

| Query | | | | Subject | score | Identities | |
|---|---|---|---|---|---|---|---|
| Name | Length | Start | End | Description | E-Value | Match/Total | Pct.(%) |
| contig00001_orf00002 | 354 | 1 | 351 | PseT.3 conserved hypothetical protein [Enterobacteria phage vB_EcoM-VR7] | 5E−42 | 110/117 | 94 |
| contig00001_orf00004 | 489 | 7 | 486 | hypothetical protein VR7_9p239 [Enterobacteria phage vB_EcoM-VR7] | 2E−82 | 152/160 | 95 |
| contig00001_orf00038 | 933 | 1 | 930 | baseplate tail tube initiator [Shigella phage SP18] | 4E−172 | 309/310 | 99 |
| contig00001_orf00047 | 465 | 1 | 462 | UvsY recombination repair and ssDNA binding protein [Shigella phage SP18] | 1E−82 | 152/154 | 98 |
| contig00001_orf00072 | 492 | 1 | 489 | small terminase protein [Enterobacteria phage vB_EcoM-VR7] | 1E−77 | 162/163 | 99 |
| contig00001_orf00074 | 801 | 1 | 798 | gp15 tail sheath stabilizer and completion protein [Enterobacteria phage vB_EcoM-VR7] | 1E−142 | 264/266 | 99 |
| contig00001_orf00066 | 261 | 1 | 135 | prohead core protein precursor to internal peptides [Shigella phage SP18] | 1E−16 | 45/45 | 100 |
| contig00001_orf00076 | 939 | 1 | 936 | gp13 neck protein [Enterobacteria phage vB_EcoM-VR7] | 3E−159 | 308/312 | 98 |
| contig00001_orf00093 | 456 | 1 | 453 | 576 conserved hypothetical protein [Enterobacteria phage vB_EcoM-VR7] | 3E−B2 | 150/151 | 99 |
| contig00001_orf00087 | 603 | 1 | 600 | gp53 baseplate wedge subunit [Enterobacteria phage vB_EcoM-VR7] | 2E−112 | 192/200 | 96 |
| contig00002_orf00005 | 456 | 1 | 453 | lysozyme [Enterobacteria phage T7] | 4E−B1 | 143/151 | 94 |
| contig00002_orf00007 | 699 | 1 | 633 | gp2.5 [Enterobacteria phage 13a] | 4E−105 | 208/211 | 98 |
| contig00002_orf00011 | 309 | 1 | 300 | gp1. 7[Enterobacteria phage 285P] | 1E−47 | 92/102 | 90 |
| contig00002_orf00035 | 1032 | 1 | 996 | gp10A [Enterobacteria phage 13a] | 1E−137 | 313/333 | 93 |
| contig00003_orf00016 | 363 | 1 | 360 | hypothetical protein SP18gp253 [Shigella phage SP18] | 3E−52 | 117/120 | 97 |
| contig00001_orf00056 | 1008 | 1 | 1005 | RNA ligase 2 [Shigella phage SP18] | 6E−172 | 321/335 | 95 |
| contig00001_orf00101 | 390 | 10 | 387 | hypothetical phage protein [Escherichia phage wV7] | 6E−56 | 120/126 | 95 |
| contig00001_orf00089 | 825 | 1 | 822 | gp2 DNA end protector protein [Enterobacteria phage vB_EcoM-VR7] | 7E−147 | 273/274 | 99 |
| contig00001_orf00019 | 348 | 1 | 345 | head assembly cochaperone with GroEL [Shigella phage SP18] | 2E−51 | 115/115 | 100 |
| contig00001_orf00008 | 906 | 1 | 903 | polynucleotide 5'-kinase and 3'-phosphatase [Shigella phage 3P18] | 1E−170 | 287/301 | 95 |
| contig00001_orf00006 | 321 | 1 | 318 | hypothetical protein EpJS10_0215 [Enterobacteria phage JS10] | 2E−50 | 102/106 | 96 |
| contig00001_orf00020 | 324 | 1 | 321 | lysis inhibition accessory protein rapid lysis phenotype [Shigella phage SP18] | 5E−53 | 105/107 | 98 |
| contig00001_orf00017 | 582 | 1 | 579 | deoxycytidylate deaminase [Enterobacteria phage vB_EcoM-VR7] | 6E−111 | 191/193 | 98 |
| contig00001_orf00081 | 870 | 1 | 867 | baseplate wedge tail fiber connector [Shigella phage SP18] | 5E−151 | 285/289 | 98 |
| contig00001_orf00013 | 360 | 1 | 357 | hypothetical protein SP18gp231 [Shigella phage SP18] | 2E−47 | 113/119 | 94 |
| contig00001_orf00037 | 324 | 1 | 321 | hypothetical protein SP18gp210 [Shigella phage SP18] | 3E−51 | 104/107 | 97 |
| contig00001_orf00079 | 666 | 1 | 663 | baseplate wedge subunit and tail pin [Shigella phage SP18] | 2E−118 | 215/221 | 97 |
| contig00002_orf00043 | 903 | 1 | 900 | exonuclease [Enterobacteria phageT7] | 6E−168 | 293/300 | 97 |
| contig00003_orf00017 | 912 | 1 | 876 | single stranded DNA binding protein [Shigella phage SP18] | 6E−145 | 287/290 | 96 |
| contig00001_orf00063 | 819 | 1 | 816 | prohead core protein [Enterobacteria phage vB_EcoM-VR7] | 5E−99 | 267/272 | 96 |
| contig00001_orf00044 | 729 | 1 | 726 | baseplate hub assembly catalyst [Shigella phage SP18] | 2E−128 | 241/242 | 99 |
| contig00001_orf00068 | 354 | 1 | 351 | head competition protein [Shigella phage SP18] | 2E−64 | 115/117 | 98 |

TABLE 2-continued

| Query | | | | Subject | score | Identities | |
|---|---|---|---|---|---|---|---|
| Name | Length | Start | End | Description | E-Value | Match/Total | Pct.(%) |
| contig00001_orf00023 | 369 | 1 | 366 | hypothetical protein SP18gp221 [Shigella phage SP18] | 4E-66 | 122/122 | 100 |
| contig00001_orf00046 | 396 | 1 | 387 | baseplate wedge subunit [Enterobacteria phage vB_EcoM-VR7] | 5E-66 | 128/129 | 99 |
| contig00001_orf00053 | 849 | 1 | 846 | head outer capsid protein [Shigella phage SP18] | 3E-141 | 268/282 | 95 |
| contig00001_orf00042 | 459 | 1 | 456 | gp28 baseplate hub distal subunit [Enterobacteria phage vB_EcoM-VR7] | 3E-83 | 150/152 | 96 |
| contig00001_orf00064 | 639 | 1 | 636 | prohead core scaffold protein and protease [Shigella phage SP18] | 4E-118 | 210/212 | 99 |
| contig00001_orf00052 | 669 | 1 | 666 | inhibitor of prohead protease gp21 [Shigella phage SP18] | 2E-91 | 206/222 | 92 |
| contig00001_orf00045 | 624 | 1 | 621 | baseplate hub subunit [Shigella phage SP18] | 4E-115 | 206/207 | 99 |
| contig00001_orf00086 | 1786 | 1 | 1785 | baseplate hub subunit and tail lysozyme [Shigella phage SP18] | 0 | 588/595 | 96 |
| contig00001_orf00094 | 366 | 1 | 363 | hypothetical protein VR7_gp156 [Enterobacteria phage vB_EcoM-VR7] | 2E-48 | 119/121 | 96 |
| contig00001_orf00016 | 336 | 1 | 333 | hypothetical protein SP18gp229 [Shigella phage SP18] | 2E-54 | 108/111 | 97 |
| contig00002_orf00043 | 408 | 1 | 406 | 4.7 protein [Enterobacteria phage T7] | 2E-54 | 123/135 | 91 |
| contig00002_orf00043 | 1023 | 1 | 1020 | DNA ligase [Enterobacteria phage T7] | 0 | 317/359 | 86 |
| contig00002_orf00043 | 1500 | 1 | 975 | gp17 [Enterobacteria phage 13a] | 6E-120 | 266/330 | 81 |
| contig00002_orf00043 | 591 | 1 | 586 | tall protein [Yersinia pestis phage phiA1122] | 2E-99 | 194/196 | 96 |
| contig00003_orf00017 | 411 | 1 | 408 | endonuclease 11 [Shigella phage SP18] | 5E-72 | 136/136 | 100 |
| contig00003_orf00017 | 861 | 1 | 858 | a TMP thymidylate synthase [Enterobacteria phage vB_EcoM-VR7] | 2E-146 | 245/286 | 85 |
| contig00003_orf00017 | 669 | 1 | 646 | loader of gp41 DNA helicase [Shigella phage SP18] | 4E-18 | 211/216 | 97 |
| contig00001_orf00110 | 306 | 1 | 303 | hypothetical protein SP18gp146 [Shigella phage SP18] | 4E-50 | 99/101 | 96 |
| contig00001_orf00058 | 1281 | 1 | 1278 | capsid vertex protein [Enterobacteria phage vB_EcoM-VR7] | 0 | 411/426 | 96 |
| contig00001_orf00041 | 1746 | 1 | 1743 | baseplate hub subunit and tail length determinator [Shigella phage SP18] | 0 | 570/581 | 98 |
| contig00001_orf00064 | 1959 | 1 | 1956 | baseplate wedge subunit [Shigella phage SP18] | 0 | 648/652 | 99 |
| contig00001_orf00060 | 1785 | 1 | 1782 | gp10 baseplate wedge subunit and tail pin [Enterobacteria phage vB_EcoM-VR7] | 0 | 563/594 | 98 |
| contig00001_orf00040 | 1095 | 1 | 1092 | baseplate tail tube cap [Shigella phage SP18] | 0 | 362/364 | 99 |
| contig00001_orf00090 | 600 | 1 | 597 | gp3 tail completion and sheath stabilizer protein [Enterobacteria phage vB_EcoM-VR7] | 2E-112 | 199/199 | 100 |
| contig00001_orf00068 | 492 | 1 | 489 | tall tube protein [Shigella phage SP18] | 2E-93 | 161/163 | 98 |
| contig00001_orf00091 | 676 | 1 | 675 | gp1 deoxynucleoside monophosphate kinase [Enterobacteria phage vB_EcoM-VR7] | 2E-127 | 222/225 | 98 |
| contig00001_orf00032 | 717 | 1 | 714 | hypothetical protein SP18gp215 [Shigella phage SP18] | 3E-128 | 235/236 | 98 |
| contig00001_orf00025 | 366 | 1 | 363 | hypothetical protein SP18gp220 [Shigella phage SP18] | 1E-66 | 120/121 | 99 |
| contig00001_orf00001 | 405 | 1 | 402 | inhibitor of host transcription [Shigella phage SP18] | 2E-61 | 131/134 | 97 |
| contig00001_orf00112 | 594 | 1 | 591 | hypothetical protein SP18gp145 [Shigella phage SP18] | 7E-100 | 193/197 | 97 |
| contig00001_orf00076 | 766 | 1 | 753 | neck protein [Enterobacteria phage vB_EcoM-VR7] | 1E-144 | 251/251 | 100 |
| contig00002_orf00006 | 456 | 1 | 453 | gp3 [Enterobacteria phage 13a] | 1E-82 | 149/151 | 98 |
| contig00002_orf00017 | 1080 | 1 | 1077 | protein kinase [Enterobacteria phage T7] | 2E-163 | 325/359 | 90 |
| contig00002_orf00024 | 360 | 1 | 357 | gp16.5 [Enterobacteria phage 13a] | 1E-57 | 112/119 | 94 |

TABLE 2-continued

| Query | | | | Subject | score | Identities | |
|---|---|---|---|---|---|---|---|
| Name | Length | Start | End | Description | E-Value | Match/Total | Pct.(%) |
| contig00002_orf00030 | 591 | 1 | 586 | internal virlon protein [Yersinia pestis phage phiA1122] | 1E-74 | 178/196 | 99 |
| contig00003_orf00009 | 582 | 1 | 579 | Frd dihydrofolate reductase [Enterobacteria phage vB_EcoM-VR7] | 6E-105 | 187/193 | 96 |
| contig00003_orf00011 | 342 | 1 | 339 | hypothetical protein SP18gp249 [Shigella phage SP18] | 3E-59 | 111/113 | 96 |
| contig00003_orf00014 | 366 | 1 | 363 | hypothetical protein SP18gp252 [Shigella phage SP18] | 2E-60 | 113/121 | 93 |

please see the [partial genome Sequence of ΦCJ20] in attachment.

Example 7

Stability Test of ΦCJ20 Depending on pH

In order to confirm whether or not the bacteriophage ΦCJ20 may have stability in a low pH environment in stomach, stability test was performed over a wide pH range (pH 3.0, 3.5, 4.0, 5.5, 6.4, 7.5, 8.3, 9.2, and 11.0).

For test, various pH solutions (sodium acetate buffer (pH 4.0, pH 5.5, and pH 6.4), sodium citrate buffer (pH 3.0 and pH 3.5), sodium phosphate buffer (pH 6.9 and pH 7.4), and Tris-HCl solution (pH 8.2, pH 9.0, pH 9.8, and pH 11.0)) were prepared at a concentration of 0.2 M, respectively.

After 180 μl of each of the pH solutions was mixed with 20 μl of bacteriophage solution having a titer of $2.1\times10^{10}$ pfu/ml so that a concentration of each of pH solution became 1 M, and each of the pH solutions was left at room temperature for 2 hours. In a control group, 20 μl of the bacteriophage solution ($2.1\times10^{10}$ pfu/ml) was mixed with 180 μl of SM solution and then left at room temperature for 2 hours. Then, the reaction solution was diluted step by step, 10 μl of the diluted solution at each step was dropped and cultured at 30° C. for 18 hours by a soft agar overlay method, and the titer was measured through the presence or absence of lysis (FIG. 4).

Figure 4:
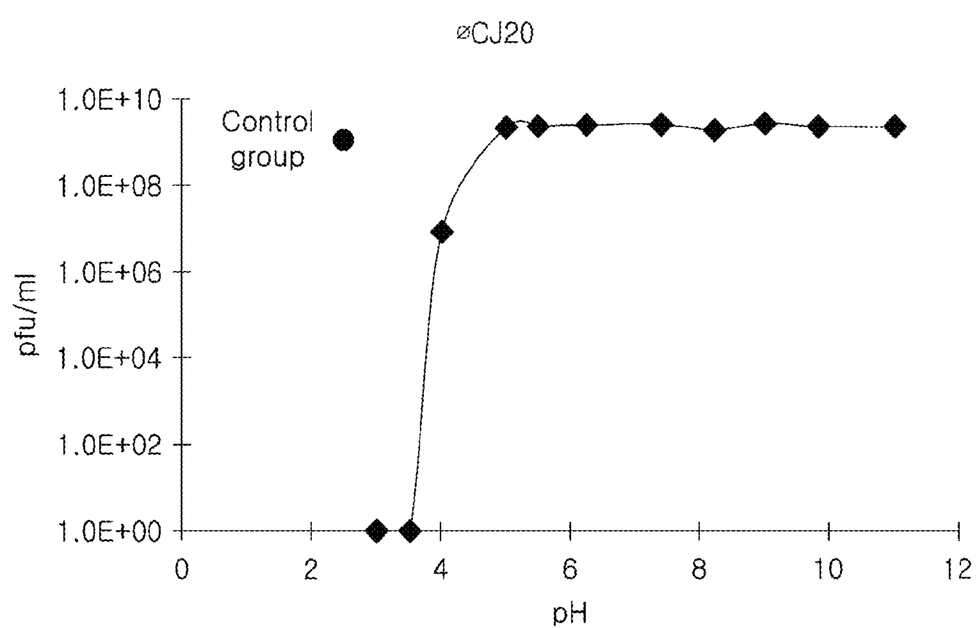
FIG. 4 is a graph showing a result of an acid resistance test of the novel bacteriophage ΦCJ20.

FIG. 4 shows a result of the acid resistance test of the bacteriophage ΦCJ20. As shown in FIG. 4, it may be confirmed that the bacteriophage ΦCJ20 did not lose its activity and was stable in a pH range of 5.0 to 11.0 as compared to the control group.

Example 8

Stability Test of ΦCJ20 Depending on Temperature

A test for confirming stability against heat generated during a formulating process of the bacteriophage in the case of using the bacteriophage as a feed additive formulation among formulations of the bacteriophage was performed.

In detail, 100 μl of bacteriophage ΦCJ20 solution having a concentration of $2.0\times10^{10}$ pfu/ml was left at 37° C., 42° C., 53° C., and 60° C. for 0, 30, 60, and 120 minutes, respectively. Then, the solutions above were diluted step by step, 10 μl of the diluted solution at each of the steps was dropped and cultured at 30° C. for 18 hours by a soft agar overlay method, and the titer was measured through the presence or absence of lysis (FIG. 5).

Figure 5:
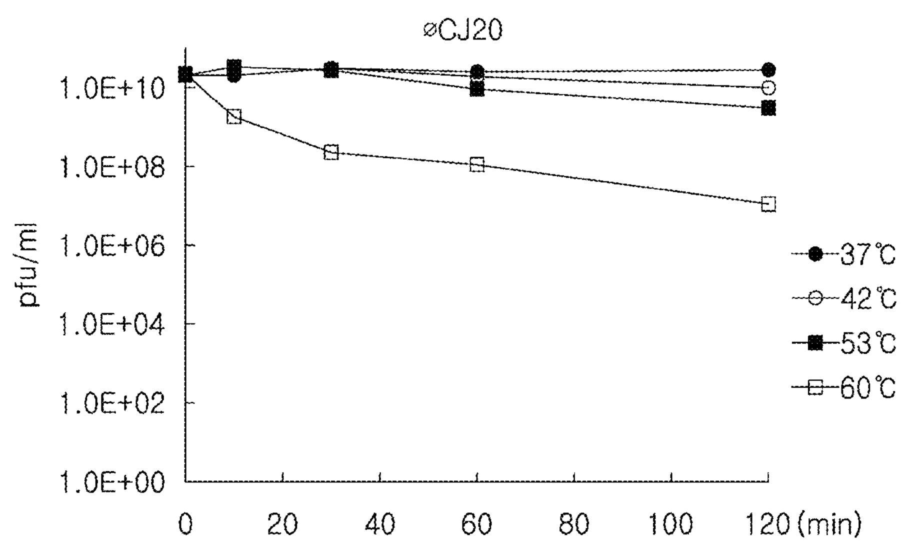
FIG. 5 is a graph showing a result of a heat resistance test of the novel bacteriophage ΦCJ20.

FIG. 5 shows a result of a heat resistance test of the bacteriophage ΦCJ20. As shown in FIG. 5, the bacteriophage ΦCJ20 maintained its activity even though exposed at 53° C. for up to 2 hours, but its activity was reduced according to the exposure time, when exposed at 60° C.

Example 9

Infection Spectrum Test of ΦCJ20 on Wild-Type Strains of ETEC

Whether or not the bacteriophage ΦCJ20 had a lytic activity was tested on 15 wild-type strains of ETEC obtained from College of Veterinary Medicine, Seoul National University and University of Guelph in Canada other than ETEC (SNU105) used in the experiment.

In detail, 10 μl of bacteriophage ΦCJ20 solution having a titer of $10^9$ pfu/ml and mixed with 150 μl of a shake culture solution ($OD_{600}$=2) of each of the strains was dropped and cultured at 30° C. for 18 hours by a soft agar overlay method. Then, whether or not a plaque was formed was observed.

The results were shown in the following Table 3.

TABLE 3

| Serotype | Strain | Plaque formation |
|---|---|---|
| ETEC | SNU345 | x |
| | SNU105 | ○ |
| | SNU0122 | x |
| | SNU0149 | ○ |
| | SNUJG280 | ○ |
| | SNUF4 | ○ |
| | SNU162 | ○ |
| | SNU160 | ○ |
| | SNU107 | ○ |
| | CANR08 | ○ |
| | SNU2618 | x |
| | SNU2617 | x |
| | SNU193 | x |
| | SNU274 | ○ |
| | SNU3220 | ○ |

As shown in Table 3, the bacteriophage showed infectivity on F-serotype K88 (SNU105, SNU107, SNU160, SNU162, SNUF4, SNU3220, CANR08, and SNUJG280) as well as ETEC 0-serotype 0149 (SNU107, SNUF4, SNUJG280, SNU3220, CANR08, and SNU0149) which is the most common cause of diarrhea in swine in general farms. Therefore, it may be expected that the bacteriophage will show excellent efficiency at the time of actually applying the bacteriophage.

The invention claimed is:

1. A method of suppressing or treating an infectious disease caused by ETEC, the method comprising:

administering bacteriophage ΦCJ20 (KCCM11362P) to an animal other than human, wherein the bacteriophage ΦCJ20 comprises nucleic acid having SEQ ID NO: 1.

2. The method according to claim 1, wherein the infectious disease is colibacillosis.

3. A method of suppressing or treating an infectious disease caused by ETEC, the method comprising:

administering a composition comprising bacteriophage ΦCJ20 (KCCM11362P) to an animal other than human wherein the bacteriophage ΦCJ20 comprises nucleic acid having SEQ ID NO: 1.

4. The method according to claim 3, wherein the infectious disease is colibacillosis.

5. A method of preparing an animal feed composition, the method comprising:

providing a bacteriophage composition comprising a bacteriophage, said bacteriophage comprising nucleic acid having SEQ ID NO: 1; and mixing the bacteriophage composition with an animal feed base to provide the animal feed composition.

6. The method of claim 5, wherein the bacteriophage composition prior to mixing is in powder or liquid, wherein the animal feed composition further comprises one or more additives selected from the group consisting of an amino acid, a vitamin, an enzyme, a probiotic, a flavoring agent, a non-protein nitrogen compound, a silicate, a buffer, a coloring agent, an extractant and an oligosaccharide.

7. A method of feeding an animal other than human, the method comprising:

providing an animal feed composition comprising a bacteriophage, said bacteriophage comprising nucleic acid having SEQ ID NO: 1; and feeding to the animal other than human the animal feed composition.

8. A method of preparing a drinking water composition, the method comprising:

providing a bacteriophage composition comprising a bacteriophage, said bacteriophage comprising nucleic acid having SEQ ID NO: 1; and mixing the bacteriophage composition with drinking water to provide the drinking water composition.

9. The method of claim 8, wherein the bacteriophage composition prior to mixing is in powder or liquid, wherein the drinking water composition further comprises one or more additives selected from the group consisting of an amino acid, a vitamin, an enzyme, a probiotic, a flavoring agent, a non-protein nitrogen compound, a silicate, a buffer, a coloring agent, an extractant and an oligosaccharide.

10. A method of feeding an animal other than human drinking water, the method comprising:

providing a drinking water composition comprising a bacteriophage, said bacteriophage comprising nucleic acid having SEQ ID NO: 1; and feeding to the animal other than human the drinking water composition.

* * * * *

UNITED STATES PATENT AND TRADEMARK OFFICE

CERTIFICATE OF CORRECTION

PATENT NO. : 9,862,935 B2
APPLICATION NO. : 14/770420
DATED : January 9, 2018
INVENTOR(S) : Eun Mi Shin et al.

It is certified that error appears in the above-identified patent and that said Letters Patent is hereby corrected as shown below:

In the Specification

At Column 1, Line 51, change “enteroinvacive” to --enteroinvasive--.

At Column 4, Line 15, change “sodiumdodecylsulfate” to --sodium dodecyl sulfate--.

At Column 5, Line 1, change “Seodamun-gu,” to --Seodaemun-gu,--.

At Column 9, Line 36, change “Samwhaw” to --Samwha--.

At Column 9, Line 37, change “Chungchong” to --Chungcheong--.

At Column 10, Line 52, change “bacteriocidal” to --bactericidal--.

At Column 10, Line 55, change “Seodamun-gu,” to --Seodaemun-gu,--.

At Column 11, Line 1, change “Rosetta (DE3),” to --Rosetta(DE3),--.

At Column 11, Line 2, change “Tuner (DE3),” to --Tuner(DE3),--.

At Column 11, Line 29, change “Rosetta (DE3),” to --Rosetta(DE3),--.

At Column 11, Line 30, change “Tuner (DE3),” to --Tuner(DE3),--.

At Column 12, Line 51, change “INC.” to --Inc.--.

At Column 12, Line 53, change “GeneMArk.hmm,” to --GeneMark.hmm,--.

At Columns 13-14, Line 7 (approx.), change “VR7_9p239” to --VR7_gp239--.

Signed and Sealed this
Eighth Day of May, 2018

Andrei Iancu
*Director of the United States Patent and Trademark Office*

At Columns 13-14, Line 24 (approx.), change “159” to --169--.

At Columns 13-14, Line 26 (approx.), change “576” to --57B--.

At Columns 13-14, Line 32 (approx.), change “4E-B1” to --4E-81--.

At Columns 13-14, Line 42 (approx.), change “6E-56” to --6E-66--.

At Columns 13-14, Line 47 (approx.), change “2E-51” to --2E-61--.

At Columns 13-14, Line 51 (approx.), change “3P18]” to --SP18]--.

At Columns 13-14, Line 60 (approx.), change “285/289” to --286/289--.

At Columns 13-14, Line 70 (approx.), change “96” to --98--.

At Columns 13-14, Line 72 (approx.), change “96” to --98--.

At Columns 13-14, Line 77 (approx.), change “contig00001_orf00068” to --contig00001_orf00088--.

At Columns 13-14, Line 77 (approx.), change “competition” to --completion--.

At Columns 15-16, Line 4, change “4E-66” to --4E-68--.

At Columns 15-16, Line 6 (approx.), change “396” to --390--.

At Columns 15-16, Line 11 (approx.), change “96” to --98--.

At Columns 15-16, Line 20 (approx.), change “1786” to --1788--.

At Columns 15-16, Line 20 (approx.), change “96” to --98--.

At Columns 15-16, Line 22 (approx.), change “96” to --98--.

At Columns 15-16, Line 27 (approx.), change “contig00002_orf00043” to --contig00002_orf0001--.

At Columns 15-16, Line 27 (approx.), change “406” to --405--.

At Columns 15-16, Line 29 (approx.), change “contig00002_orf00043” to --contig00002_orf00013--.

At Columns 15-16, Line 29 (approx.), change “86” to --88--.

At Columns 15-16, Line 31 (approx.), change “contig00002_orf00043” to --contig00002_orf00027--.

At Columns 15-16, Line 32 (approx.), change “contig00002_orf00043” to --contig00002_orf00033--.

At Columns 15-16, Line 32 (approx.), change “tall” to --tail--.

At Columns 15-16, Line 32 (approx.), change “96” to --98--.

At Columns 15-16, Line 34 (approx.), change “contig00003_orf00017” to --contig00003_orf0003--.

At Columns 15-16, Line 34 (approx.), change “11” to --II--.

At Columns 15-16, Line 36 (approx.), change “contig00003_orf00017” to --contig00003_orf0008--.

At Columns 15-16, Line 39 (approx.), change “contig00003_orf00017” to --contig00003_orf00019--.

At Columns 15-16, Line 41 (approx.), change “96” to --98--.

At Columns 15-16, Line 46 (approx.), after “subunit” delete “and”.

At Columns 15-16, Line 49 (approx.), change “contig00001_orf00064” to --contig00001_orf00084--.

At Columns 15-16, Line 51 (approx.), change “contig00001_orf00060” to --contig00001_orf00080--.

At Columns 15-16, Line 59 (approx.), change “tall” to --tail--.

At Columns 15-16, Line 73 (approx.), change “contig00001_orf00076” to --contig00001_orf00075--.

At Columns 15-16, Line 73 (approx.), change “766” to --786--.

At Columns 17-18, Line 4 (approx.), change “virlon” to --virion--.

At Columns 17-18, Line 4 (approx.), change “99” to --90--.

At Columns 17-18, Line 9 (approx.), change “96” to --98--.

In the Claims

At Column 77, Line 43 (approx.), in Claim 3, change “human” to --human,--.